(12) United States Patent
Boyce

(10) Patent No.: US 11,958,859 B2
(45) Date of Patent: Apr. 16, 2024

(54) USE OF PYRIDOXAL ACETAL SALTS AS WATER-TRIGGERED PRO-FRAGRANCES

(71) Applicant: Florida Gulf Coast University Board of Trustees, Fort Meyers, FL (US)

(72) Inventor: Gregory R. Boyce, Estero, FL (US)

(73) Assignee: Florida Gulf Coast University Board of Trustees, Fort Myers, FL (US)

( * ) Notice: Subject to any disclaimer, the term of this patent is extended or adjusted under 35 U.S.C. 154(b) by 932 days.

(21) Appl. No.: 16/964,804

(22) PCT Filed: Jan. 24, 2019

(86) PCT No.: PCT/US2019/014864
§ 371 (c)(1),
(2) Date: Jul. 24, 2020

(87) PCT Pub. No.: WO2019/147742
PCT Pub. Date: Aug. 1, 2019

(65) Prior Publication Data
US 2021/0053980 A1  Feb. 25, 2021

Related U.S. Application Data

(60) Provisional application No. 62/622,175, filed on Jan. 26, 2018.

(51) Int. Cl.
| | |
|---|---|
| *C07D 491/048* | (2006.01) |
| *A23G 4/08* | (2006.01) |
| *A61K 8/06* | (2006.01) |
| *C07C 57/44* | (2006.01) |
| *C07C 309/17* | (2006.01) |

(52) U.S. Cl.
CPC .......... *C07D 491/048* (2013.01); *A23G 4/08* (2013.01); *A61K 8/06* (2013.01); *C07C 57/44* (2013.01); *C07C 309/17* (2013.01)

(58) Field of Classification Search
CPC ................................................ C07D 491/048
See application file for complete search history.

(56) References Cited

U.S. PATENT DOCUMENTS 2,519,469 A * 8/1950 Heyl .................... C07D 491/04
546/116
3,573,286 A    3/1971 Zenno et al.

OTHER PUBLICATIONS

Herrmann; Angew. Chem. Int. Ed. 2007, 46, 5836-5863. https://doi.org/10.1002/anie.200700264 (Year: 2007).*
Yazarians; Tetrahedron Letters 2017, 58, 2258-2260. http://dx.doi.org/10.1016/j.tetlet.2017.04.082 (Year: 2017).*
Kibardina et al., "Reaction of Pyridoxal with Hydrophosphoryl Compounds," Heteroatom Chemistry, vol. 27, No. 4, pp. 221-227, Jul. 2016.
Nagata et al., "Solvolysis of Pyridoxal Hydrochloride in Alcohols," Chem. Pharm. Bull., vol. 41, No. 6, pp. 1019-1022, Jun. 1993.
Supplementary European Search Report issued in application No. EP19744579 dated Sep. 21, 2021.
Weeks et al., "Utilization of pyridoxal acetal salts as water-triggered, slow-release pro-fragrances," New Journal of Chemistry, vol. 42, No. 19, Jul. 2018.
International Search Report issued for application No. PCT/US2019/014864 dated Jun. 11, 2019.
Pubchem, CID 110791, pp. 1-7, Aug. 8, 2005, Retrieved from the Internet: https://pubchem.ncbi.nlm.nih.gov/compound/110791.
Pubchem, CID 129752673, pp. 1-6, Sep. 13, 2017, Retrieved from the Internet: https://pubchem.ncbi.nlm.nih.gov/compound/129752673.
Pubchem, CID 129752674, pp. 1-5, Sep. 13, 2017, Retrieved from the Internet: https://pubchem.ncbi.nlm.nih.gov/compound/129752674.
Pubchem, CID 85848286, pp. 1-7, Nov. 3, 2014, Retrieved from the Internet: https://pubchem.ncbi.nlm.nih.gov/compound/85848286.
Gunaratne et al., "Pro-fragrant ionic liquids with stable hemiacetal motifs: water-triggered release of fragrances," Chem. Comm., vol. 51, pp. 4455-4457, 2015.
Kibardina et al., "Phosphorus-containing salts derived from pyridoxal," Russian Journal of Organic Chemistry, vol. 51, No. 10, pp. 1510-1512, 2015.

* cited by examiner

*Primary Examiner* — Daniel R Carcanague
(74) *Attorney, Agent, or Firm* — Rouget F. Henschel; Potomac Law Group, PLLC

(57) ABSTRACT

A pro-fragrance delivery system based on a vitamin scaffold and a fragrant alcohol. The vitamin scaffold may be a vitamer of vitamin B6 or derivatives thereof. The pro-fragrance releases the fragrant alcohol by action of water at neutral pH.

33 Claims, 19 Drawing Sheets

USE OF PYRIDOXAL ACETAL SALTS AS WATER-TRIGGERED PRO-FRAGRANCES

The invention relates to pro-fragrance delivery systems. In particular, the invention relates to a pro-fragrance delivery system based on a vitamin scaffold.

Volatile organic compounds (VOCs) function as signaling compounds in nature and are utilized in a myriad of everyday items including personal care products, detergents, and perfumes. The ability to preserve a fragrance for a long period of time while allowing for its continued release is challenging due to the efficient evaporation of these molecules. The delivery of VOCs in consumer products is commonly accomplished by encapsulation in designed matrices and polymers or in oil-in-water emulsions in order to preserve the longevity of the fragrance. These physical release systems rely on slow diffusion or via the breaking or dissolving of a capsule.

A drawback of the polymer systems is the low mass economy and typically low biodegradability. Cyclodextrin derivatives have also been studied for fragrancy delivery; however their utility is limited by high substrate specificity.

An alternative approach to the controlled delivery of VOCs is via chemical release using a class of compounds called pro-fragrances. A. Herrmann, *Angew. Chem. Int. Ed.*, 2007, 46, 5836. In these systems, a substrate is covalently bound to a host molecule then selectively cleaved in the presence of a specific stimuli. In consumer products, the VOC release must occur under mild conditions, usually thermally, photochemically, or enzymatically. Fragrant alcohols have been delivered as pro-fragrance esters that release in the presence of a lipase enzyme (M. Blesic et al., *RSC Adv.*, 2013, 3, 239; V. Athawale et al., *Tetrahedron Lett.*, 2002, 43, 4797; F. Aulenta et al., *Molecules*, 2005, 10, 8) or when exposed to a high pH (J.-Y. Saint Laumer et al., *Helv. Chim. Acta*, 2003, 86, 2871; A. D. Headley et al., *J. Org. Chem.*, 1994, 59, 8040; (c) S. Espinosa et al., Anal. Chem., 2002, 74, 3809). Recently, Gunaratne and coworkers developed an ionic liquid class of materials that release fragrant alcohols from a stable hemiacetal in the presence of neutral water. H. Q. N. Gunaratne et al., *Chem. Commun.*, 2015, 51, 4455. This was noteworthy as these ionic liquid materials could likely respond to atmospheric humidity which would make it useful for air fresheners or perspiration which would make it useful in personal care products.

Known pro-fragrances release under oxidation, thermolysis, photolysis, enzymatically, or via pH change. There are relatively few that release in the presence of neutral water, but these are based solely on ionic liquids. Ionic liquids have the drawbacks of being toxic and raising concerns about their impact on the environmental.

Consumers are more and more desirous of products that are natural, low-toxicity, and eco-friendly, particularly if applied to the skin or hair. Consumers especially desire products based on vitamins. Thus, a need exists for such products. In particular, a need exists for a bio-based pro-fragrance that could also be triggered by water without the need for a pH change from a vitamin-based scaffold.

SUMMARY

The pro-fragrances described herein in salt form may also be in the form of the corresponding free bases. In one embodiment, the pro-fragrance is a compound of formula I:

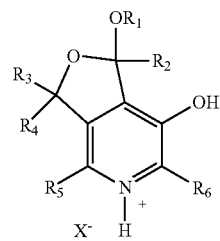

wherein $R_1$ is a C1-C20 hydrocarbyl group, and R2, R3, R4, R5, and R6 are independently hydrogen or a C1-C10 hydrocarbyl group; and X is a counterion. Alternatively, the pro-fragrance is the corresponding free base (i.e., omitting HX).

$R_1$ may be any group that corresponds to an alcohol $R_1$—OH having aroma improving qualities when applied to a subject. For example, alcohol $R_1$—OH is preferably a fragrant alcohol. Examples include 2-phenylethanol, geraniol, majantol, and menthol. $R_2$, $R_3$, $R_4$, and $R_5$ are chosen to provide a scaffold suitable for releasing alcohol $R_1$—OH according to the invention, to provide aroma improving qualities when applied to a subject.

In one embodiment, when $R_6$ is methyl and $R_2$, $R_3$, $R_4$, and $R_5$ are each hydrogen, then $R_1$ is not C1-C4 alkyl, and preferably $R_1$ is not C1-C3 alkyl.

In another embodiment, $R_6$ is C1-C6 straight, branched, or cyclic alkyl. In a preferred embodiment $R_6$ is methyl.

In another embodiment, the compound is of formula II:

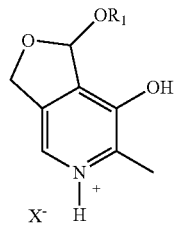

wherein $R_1$ is a C5-C20 hydrocarbyl group.

The counterion X may be any anion suitable for use in skin care, hair care, or cosmetics, or other field of use wherein a subject is provided with an improved aroma. Alternatively, the pro-fragrance is the corresponding free base (i.e., omitting HX).

The compound is preferably in the form of a composition with at least one carrier, adjuvant, or active agent suitable for skin care, hair care, or cosmetics. Such compositions may be, as non-limiting examples, emulsions, pastes, and creams as suitable for personal use products. Examples of personal use products include, but are not limited to, perfumes, colognes, pre-shave and after-shave products, deodorants, antiperspirants, moisturizing lotion, tanning/sunscreen lotions, and make-up products.

The composition may have a neutral pH, for example, a pH of 6.5-7.5, 6.7-7.3, 6.9-7.1, or about 7.

In an embodiment, the compound of formula I or II (or the corresponding free base of the compound of formula I or II) wherein $R^1$ is a radical that results when ROH is one of the following alcohols:

(−)-3-Neoisothujanol; (−)-Thujol (21653-20-3); (−)-Sclareol (515-03-7); (+)-Cedrol (77-53-2); (+/−)-2,4,8-Trimethyl-7-nonen-2-ol (437770-28-0); (+/−)-2-Methyl-1-butanol (137-32-6); (+/−)-4-Mercapto-4-methyl-2-pentanol (31539-84-1); (+/−)-trans- and cis-4,8-Dimethyl-3,7-nonadien-2-ol (67845-50-5); (E)-2-Decenol (18049-18-2); (E)-2-Octen-1-ol (18409-17-1); (E)-2-Octen-4-ol (20125-81-9); (E)-3-(Z)-6-Nonadien-1-ol (56805-23-3); (E,E)-2,4-Decadien-1-ol (18409-21-7); (E,E)-2,4-Hexadien-1-ol (1 11-28-4); (E,R)-3,7-Dimethyl-1,5,7-octatrien-3-ol (20053-88-7); (R)-(−)-1-Octen-3-ol (3687-48-7); (Z)(Z)-3,6-Nonadien-1-ol (53046-97-2); (Z)-2-Hexen-1-ol (928-94-9); (Z)-4-Hepten-1-ol (6191-71-5); 10, 11-Dihydrofarnesol (7226-86-0); 1-Decen-3-ol (51 100-54-0); 1-Hexen-3-ol (4798-44-1); 1-Octanol (1 11-87-5); 1-Octen-3-ol (3391-86-4); 1-Penten-3-ol (616-25-1); 1-Phenyl-1-propanol (93-54-9); 2(10)-Pinen-3-ol (5947-36-4); 2,3-Dihydrofarnesol (51411-24-6); 2,6-nonadienol (28069-72-9); 2-Ethyl-1-hexanol (104-76-7); 2-Ethyl-fenchol (18368-91-7); 2-Heptanol (543-49-7); 2-Hexen-1-ol (2305-21-7); 2-Methyl-4-phenyl-2-butanol (103-05-9); 2-Nonanol (628-99-9); 2-Octanol (123-96-6); 2-Phenoxy ethanol (122-99-6); 2-Undecanol (1653-30-1); 2-Undecen-1-ol (37617-03-1); 3,5,5-Trimethyl-1-hexanol (3452-97-9); 3,7-Dimethyl-1-octanol (106-21-8); 3-Decanol (1565-81-7); 3-Heptanol (589-82-2); 3-Octanol (589-98-0); 3-Octen-2-ol (76649-14-4); 3-Phenyl-1-propanol (122-97-4); 4-Hexen-1-ol (6126-50-7); 4-Phenyl-2-butanol (2344-70-9); 4-Phenyl-3-buten-2-ol (17488-65-2); 4-Thujanol; Sabinene hydrate (546-79-2); 5-Phenylpentanol (10521-91-2); 6,7-Dihydrofarnesol (92857-01-7); 6-Hydroxydihydrotheaspirane (65620-50-0); 9-Decenol (13019-22-2); alpha, alpha-Dimethylphenethyl alcohol (100-86-7); alpha-Amylcinnamyl alcohol (101-85-9); alpha-Bisabolol (515-69-5); alpha-isobutylphenethyl alcohol (7779-78-4); alphalonol (25312-34-9); alpha-Propylphenethyl alcohol (705-73-7); alpha-Santalol (1 15-71-9); alpha-Terpineol (98-55-5); 1-(2-Tert-butylcyclohexyl)oxybutan-2-ol (139504-68-0); beta-Ionol (22029-76-1); beta-Methylcrotyl alcohol; 2-Methyl-but-2-en-1-ol (4675-87-0); beta-Methylphenethyl alcohol (1 123-85-9); ethyl 6-(acetyloxy)hexanoate (104986-28-9); Borneol (507-70-0); Caryophyllene alcohol (4586-22-5); Cinnamyl alcohol (104-54-1); cis,trans-2-Methyl-2-vinyl-5-(2-hydroxy-2-propyl)tetrahydrofuran (5989-33-3); cis-2,8-p-Menthadien-1-ol (22771-44-4); cis-2-Nonen-1-ol (41453-56-9); cis-3-Hexen-1-ol (928-96-1); cis-3-Nonen-1-ol (10340-23-5); cis-3-Octen-1-ol (20125-84-2); cis-4-Decenol (57074-37-0); cis-5-Octen-1-ol (64275-73-6); cis-6-Nonen-1-ol (35854-56-5); cis-9-Octadecenol (143-28-2); Cubebol (23445-02-5); 2-trans, 6-cis-nonadienol (7786-44-9); Decanol (1 12-30-1); Dihydro linalool (2270-57-7); Dihydro myrcenol (18479-58-8); Dihydro-beta-ionol (3293-47-8); di-Citronellol (106-22-9); (Z)-3-methyl-5-(2,2,3-trimethyl-1-cyclopent-3-enyl)pent-4-en-2-ol (67801-20-1); Ethyl linalool (10339-55-6); Farnesol (4602-84-0); Fenchyl alcohol (1632-73-1); Geraniol (106-24-1); Heptanol (1 11-70-6); Hexanol (1 11-27-3); Hydroxycitronellal diethyl acetal (7779-94-4); Hydroxycitronellal dimethyl acetal (141-92-4); Hydroxycitronellal propyleneglycol acetal (93804-64-9); Isoborneol (124-76-5); Isobutanol (78-83-1); 1-methyl-2-1,2,2-trimethyl-3-bicyclo[3.1.0]hexanyl]methyl]cyclopropyl] methanol (198404-98-7); Lauryl alcohol (1 12-53-8); Linalool (78-70-6); Linalool oxide pyranoid (14049-11-7); Mayol (5502-75-0); Nerol; (Z)-Geraniol (106-25-2); Nerolidol; FCI-1 19b (7212-44-4); Nonanol; Nonyl alcohol (143-08-8); Patchouli alcohol (5986-55-0); p-Cymen-8-ol; NSC-361057 (1197-01-9); Phenethylmethylethylcarbinol (10415-87-9); p-Menth-1-en-9-ol (18479-68-0); Phenyl ethyl alcohol (60-12-8); (E)-3,3-Dimethyl-5-(2,2,3-trimethyl-3-cyclopenten-1-yl)-4-penten-2-ol (107898-54-4); Prenol; Prenyl alcohol (556-82-1); (E)-2-ethyl-4-(2,2,3-trimethyl-1-cyclopent-3-enyl)but-2-en-1-ol (28219-61-6); Rhodinol (6812-78-8); m-(isocamphyl-5)cyclohexanol (66068-84-6); Tetrahydrolinalool (78-69-3); trans- and cis-2,4,8-Trimethyl-3,7-nonadien-2-ol (479547-57-4); trans-2-Nonen-1-ol (31502-14-4); trans-2-trans-4-Heptadien-1-ol (33467-79-7); trans-3-Hexenol (928-97-2); Undecyl alcohol (1 12-42-5); 4-methyldec-3-en-5-ol (81782-77-6); Verbenol; (+)-Verbenol (473-67-6); or Vetiverol (89-88-3).

Another embodiment is a method of providing a scent to a subject administering to a subject an effective amount of the pro-fragrant compounds disclosed above (as salt or free base) or a corresponding composition. The scent may be released in a timed-release manner, preferably over, e.g., 2-48 hours, 4-36 hours, or 8-24 hours. The compounds disclosed herein may also be used as pro-flavor compounds in products such as chewing gum.

Certain embodiments of the invention may be obtained by a high-yielding, one-step synthesis of pyridoxal acetal salts. This embodiment is a cost-effective, bio-based material for the slow release of alcohols in the presence of water. For some embodiments, the rate of release is proportional with the concentration of water in time-dependent NMR studies. Certain embodiments of pyridoxal acetal provided controlled-release with no discernible loss to side reactions over a 22-hour period. This delivery system is useful in personal care products where perspiration could trigger the fragrance release.

BRIEF DESCRIPTION OF THE FIGURES

FIG. 12 contains $^1H$ and $^{13}C$ spectra of compound 3a.

DETAILED DESCRIPTION

Figure 1:
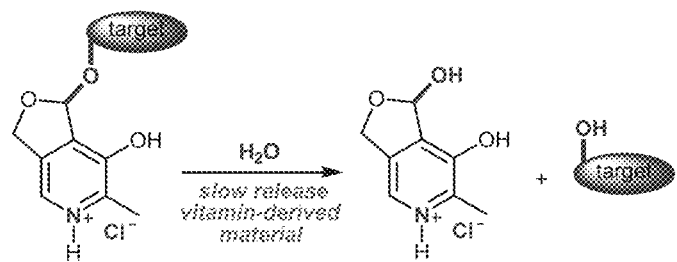
FIG. 1 shows how an embodiment of the pro-fragrance releases the target fragrance by action of water, e.g., by hydrolysis.

Those skilled in the art will understand that this invention may be embodied in many different forms and should not be construed as limited to the embodiments set forth in this application. Rather, these embodiments are provided so that this disclosure will fully convey the invention to those skilled in the art. Many modifications and other embodiments of the invention will come to mind in one skilled in the art to which this invention pertains having the benefit of the teachings presented herein.

"Hydrocarbyl" means any univalent radical, derived from a hydrocarbon. This includes a branched, unbranched, or cyclic hydrocarbon of 1-20 carbon atoms. Representative examples include, but are not limited to methyl, ethyl, n-propyl, iso-propyl, n-butyl, sec-butyl, iso-butyl, tert-butyl, n-pentyl, 2-phenylethyl, and n-decyl and the like.

"Aryl" means monocyclic or polycyclic aromatic ring systems, including fused aromatic ring systems. Representative examples include, but are not limited to, phenyl, naphthyl, anthryl, and the like. The term "aryl" is intended to include both substituted and unsubstituted aryl rings.

A "carrier" or "adjuvant" includes any additive used for personal care products, e.g., an oil, treated water, emollient, soap, detergent, surfactant, emulsifier, thickening agent, mineral powder, dye or other colorant, pigment, fragrance, wax, or stabilizer. Examples of specific ingredients include, but are not limited to, petroleum jelly, lanoline, polyethylene glycol, alcohols, or transdermal enhancers. Additional active agents may be included, e.g., any medicinal or therapeutic agents, anti-aging or anti-wrinkle agents, deodorants, anti-perspirants, astringents, or hair treatments. The composition is preferably suitable for topical application to the skin, e.g., as an ointment, cream, lotion, paste, gel, spray, aerosol, or oil. Veterinary use is also contemplated.

A fragrance or Perfume Raw Material (PRM) relates to a compound that is used to provide a pleasant odor and fragrance profile to a material. These include known natural oils that can be found in journals commonly used in the field, such as "Perfume and Flavorist" or "Journal of Essential Oil Research" or reference texts such as S. Arctander, "Perfume and Flavor Chemicals", 1969, Montclair, N.J., USA, republished by Allured Publishing Corporation Illinois (1994).

This disclosure relates to the utilization of pyridoxal acetal salts as bio-based pro-fragrances that are released in the presence of water at neutral pH. This delivery system conforms to the pro-fragrance desired traits of precursor stability, biodegradability, and cost efficiency as described by Hermann. The present invention is preferably a vitamin-based pro-fragrance. For example, vitamin B6 is an essential nutrient consisting of several vitamers as illustrated in Scheme 1 including pyridoxal, pyridoxine, pyridoxamine, and their phosphorylated derivatives.

Scheme 1. Vitamers of Vitamin $B_6$

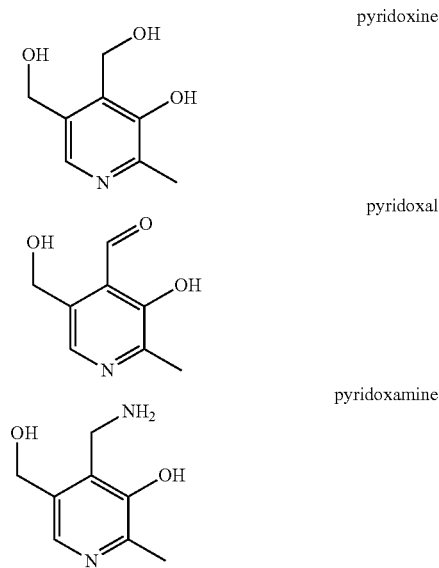

While pyridoxine HCl is the most common form of the vitamin Be complex found in dietary supplements and in treatments for various skin conditions, pyridoxal 5'-phosphate is the active form of the vitamin. S. Mooney et al., *Molecules,* 2009, 14, 329; H. Hellmann et al., *Molecules,* 2010, 15, 442. The vitamers of vitamin B can interconvert in biological systems to generate pyridoxal 5'-phosphate, which is a cofactor in over 100 enzyme-catalyzed reactions involved in metabolism and regulatory functions.

Pyridoxal HCl and pyridoxine have been known to undergo ortho-pyridinone methide chemistry for decades (D. Heyl et al., *J. Am. Chem. Soc.,* 1951, 73, 3430; A. Pocker, *J. Org. Chem.,* 1973, 38, 4295); however, this reactivity has received little attention. L. K. Kibardina et al., *Synthesis,* 2015, 47, 721; (b) L. K. Kibardina et al., *Russ. J. Gen. Chem.,* 2015, 85, 514; L. K. Kibardina et al., *Heteroat. Chem.,* 2016, 27, 221. Recently, we reported a study on the catalyst-free, regioselective etherification of pyridoxine (J. A. Yazarians et al., *Tetrahedron Lett.,* 2017, 58, 2258), although the reaction suffers from long reaction times and high temperatures. While commonly drawn as the aldehyde tautomer, pyridoxal HCl exists as the furopyridine 1 as illustrated in Scheme 2.

Scheme 2.
Pyridoxal acetal generation via a secondary ortho-pyridinone methide intermediate.

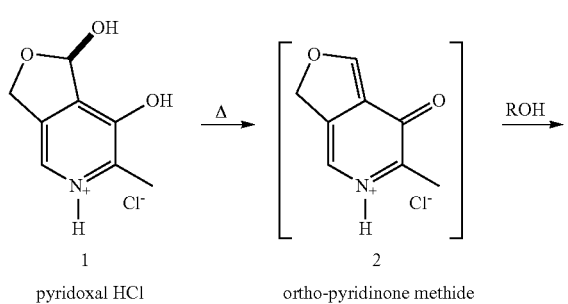

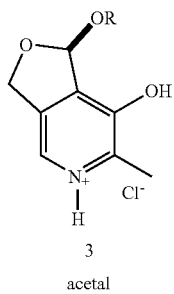

3
acetal

This tautomer enables pyridoxal HCl to undergo ortho-pyridinone methide formation through 2 under mild conditions due to the stability imparted by the dihydrofuran moiety as compared to the primary alcohol of pyridoxine. Once the ortho-pyridinone methide 2 is generated, oxa-Michael addition of the alcohol occurs to provide the pyridoxal acetal salt 3.

A series of conditions were screened to determine the optimal parameters for the purpose of avoiding the need for purification. Exposing pyridoxal HCl to the desired alcohol at 60° C. in the absence of catalyst provided clean conversion to the acetal in quantitative yields as illustrated in Scheme 3. For volatile alcohols, the solvent was evaporated to provide analytically pure product, 3a and 3c. Geraniol and 2-phenylethanol were used as substrates due to their use as fragrances in industry. Any other fragrant alcohols could be used. With respect to 2-phenylethyl acetal 3b and the geranyl acetal 3d, diethyl ether was added to the reaction mixture to precipitate the acetal that was then isolated by filtration.

Scheme 3. Synthesis of pyridoxal acetals 3a-3d.

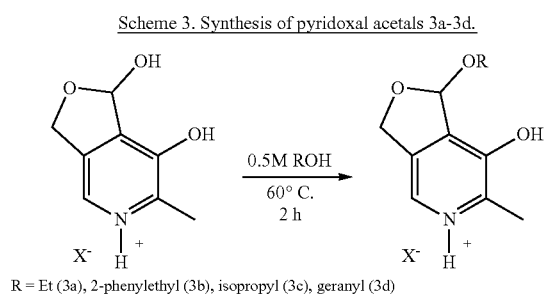

R = Et (3a), 2-phenylethyl (3b), isopropyl (3c), geranyl (3d)

Figure 2:
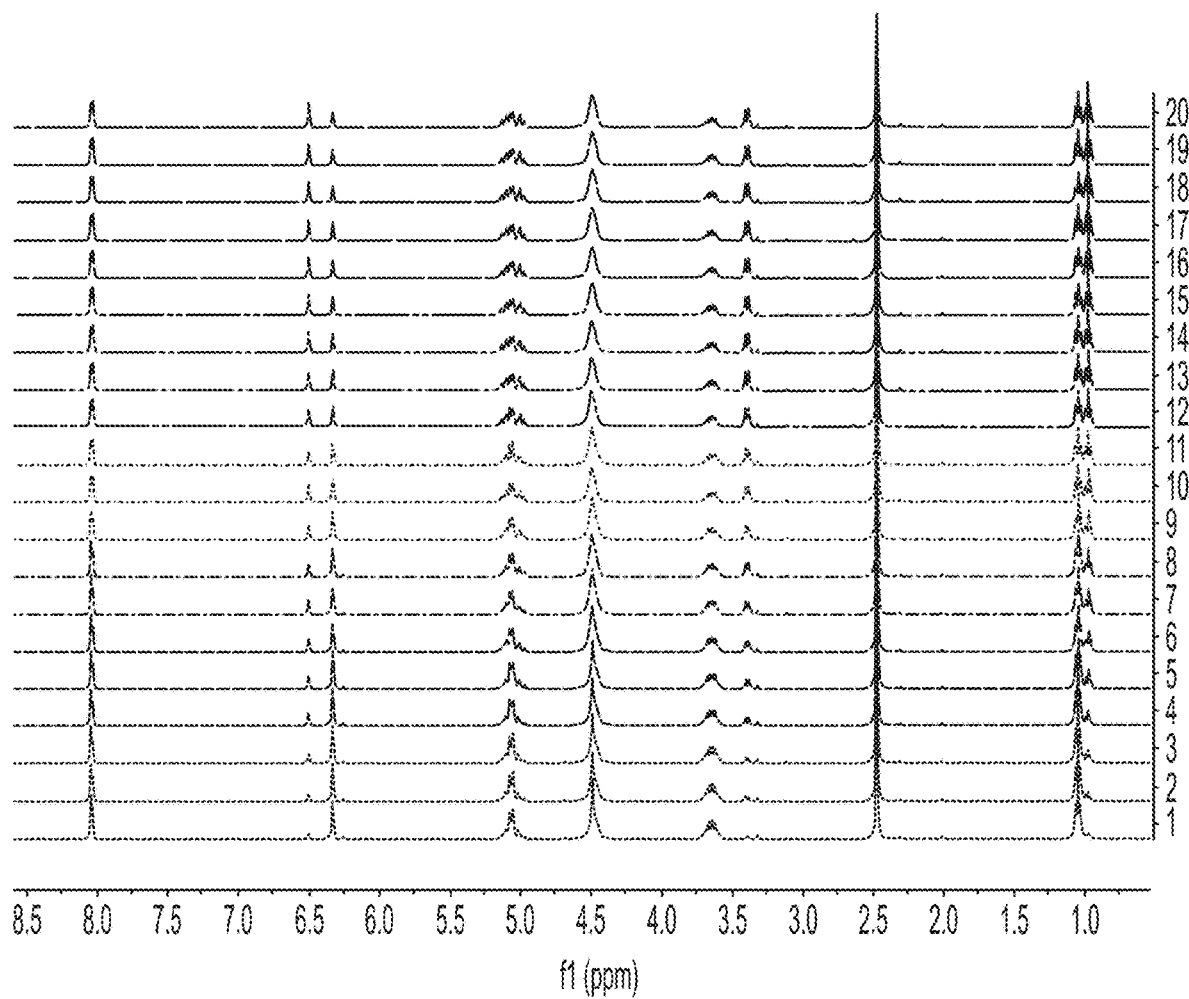
FIG. 2 is a stack plot of H NMR spectra per hour (y-axis) demonstrating the release of ethanol in the presence of deuterium oxide at a concentration of 0.2 M in DMSO-$d_6$/$D_2O$ (50:50; v/v).

The hydrolysis of the target alcohol from the pyridoxal acetal salt in the presence of $D_2O$ was monitored by $^1H$ NMR spectroscopy. This was accomplished by comparing the formation of hemiacetal C—H peak to the loss of the acetal C—H peak. For substrate 3a, the integration of the acetal C—H peak at 6.58 ppm was compared to the integration of the pyridoxal hemiacetal C—H peak at 6.41 ppm hourly to determine conversion. A stack plot of the NMR spectra for 50% $D_2O$ solution in DMSO-$d_6$ over 20 hours is illustrated in FIG. 2.

Figure 3:
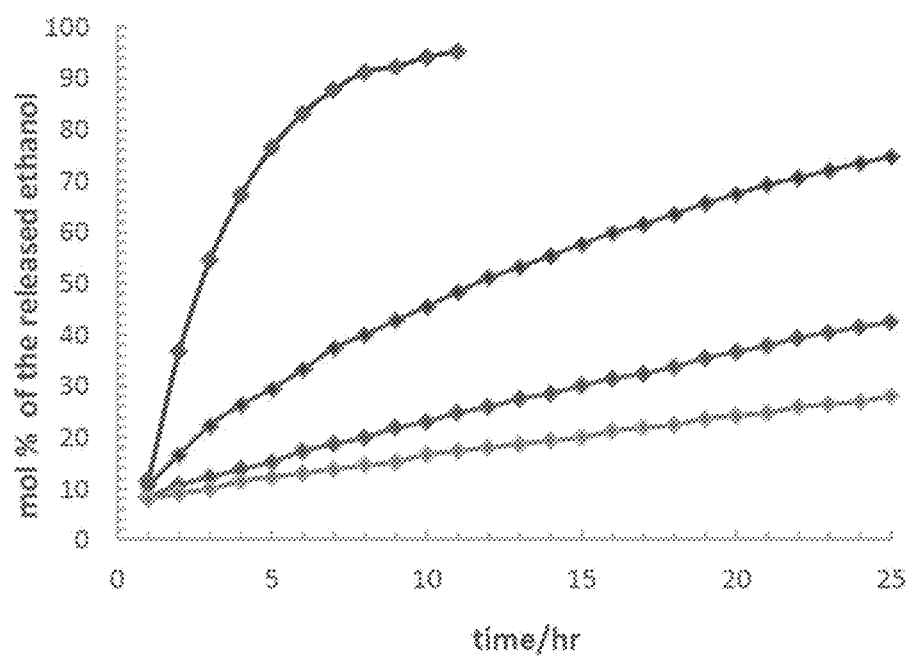
FIG. 3 is a graph showing a kinetic reaction profile for the release of ethanol from 3a at varying concentrations in DMSO-$d_6$/$D_2O$. The $D_2O$ concentrations are 25% (green), 35% (blue), 50% (red), and 100% (violet) (colors from bottom to top).

To determine the kinetics of the hydrolysis with respect to the concentration of water, acetal 3a was exposed to varying concentrations of $D_2O$ The release of ethanol from 3a was measured at concentrations of 25%, 35%, 50%, and 100% $D_2O$ in DMSO-$d_6$ and is plotted in FIG. 3. The plot demonstrates the controlled release of ethanol where the rate increases with higher concentrations of $D_2O$. The 100% $D_2O$ trial provides full cleavage after 10 hours whereas a lowest concentration of $D_2O$ (25%) provides the slowest release at only 28% cleaved after 25 hours. The 50% $D_2O$ trial provided 74% release after 25 hours and the 35% $D_2O$ trial provided 42% release.

Figure 4:
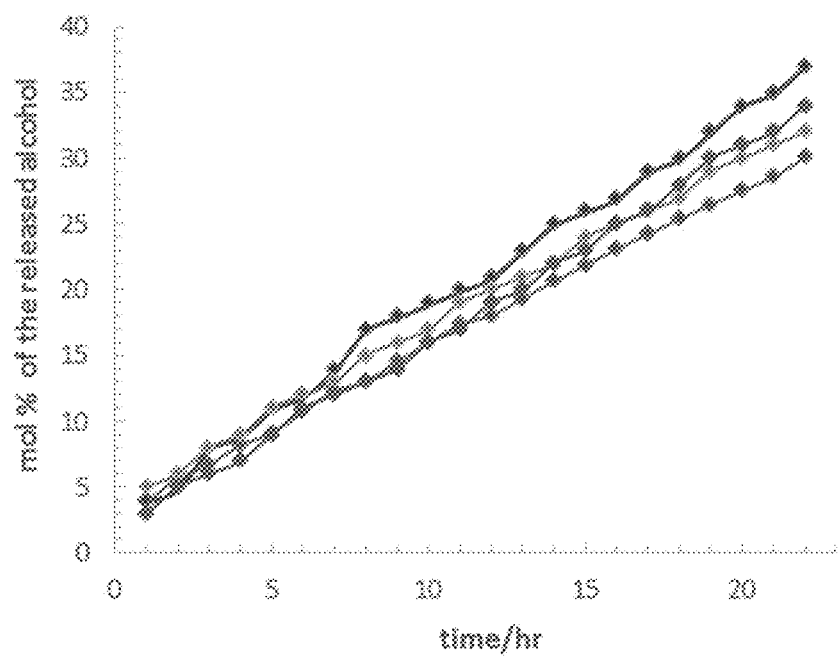
FIG. 4 is a graph showing time-dependent release of ethanol (blue), 2-phenylethanol (green), isopropanol (red) (colors at left of graph from bottom to top) from the pyridoxal acetal salts in 0.2 M DMSO-$d_6$/$D_2O$ (70:30; v/v).
Figure 5:
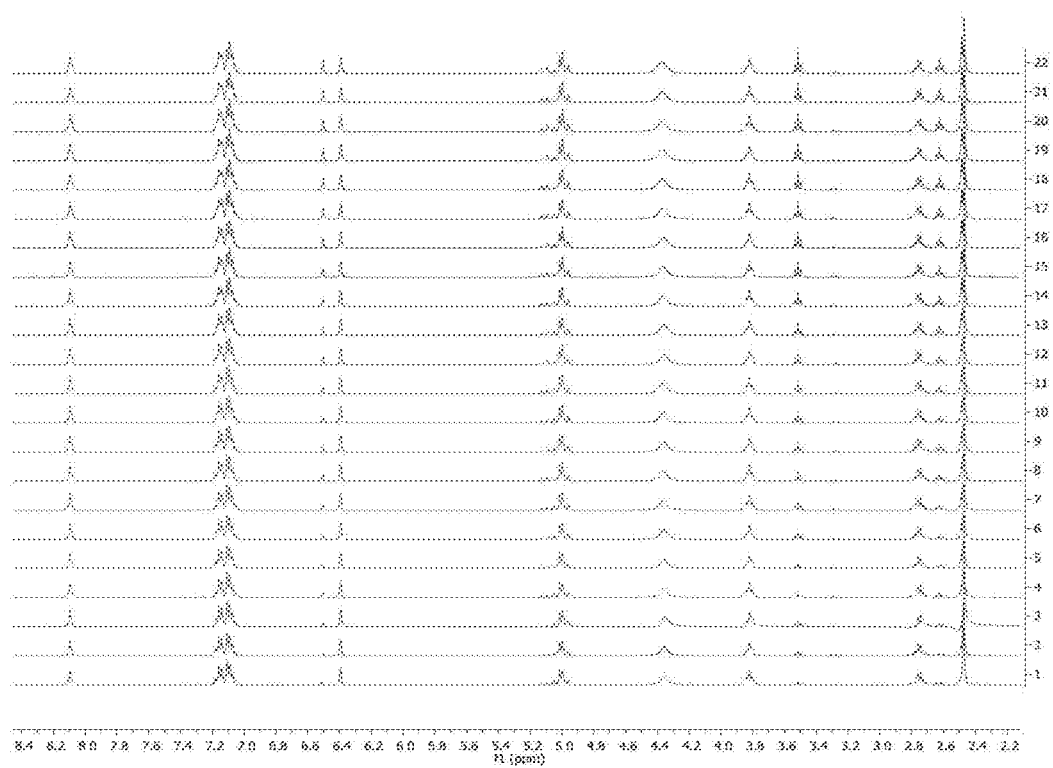
FIG. 5 is a stack plot for 2-phenylethoxy acetal showing release of 2-phenylethanol in 30% deuterium oxide in DMSO-$d_6$.
Figure 6:
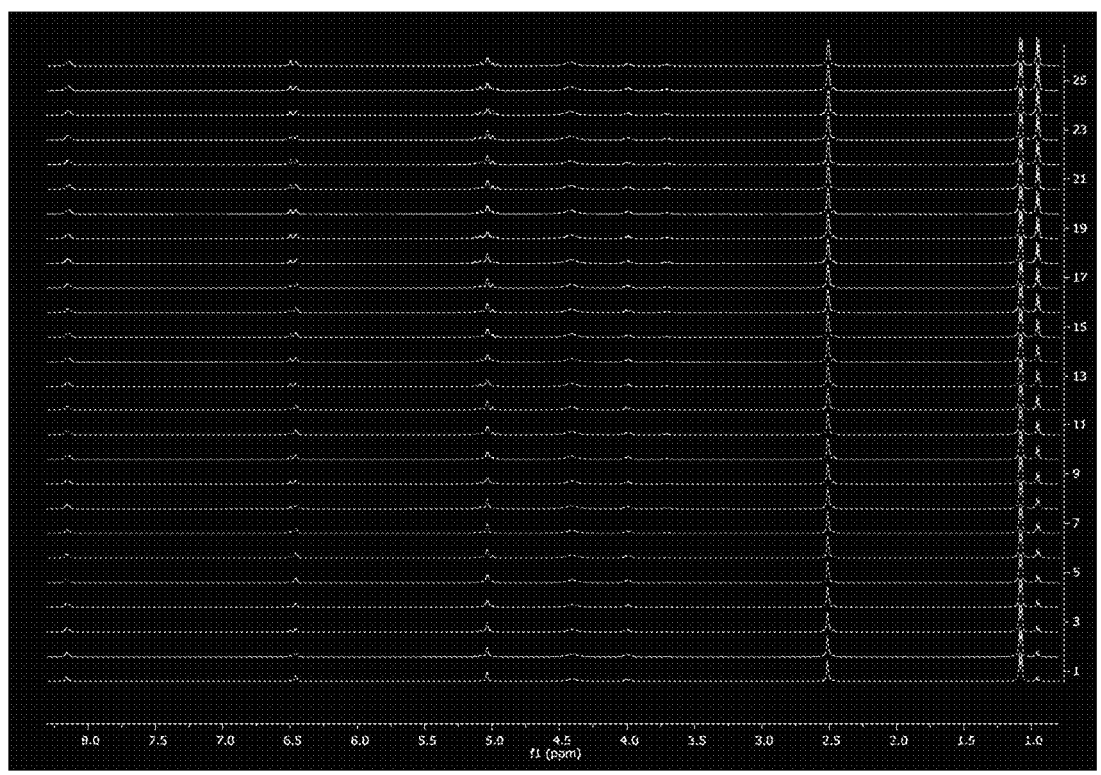
FIG. 6 is a stack plot for isopropoxy acetal showing release of isopropanol in 30% deuterium oxide in DMSO-$d_6$.
Figure 7:
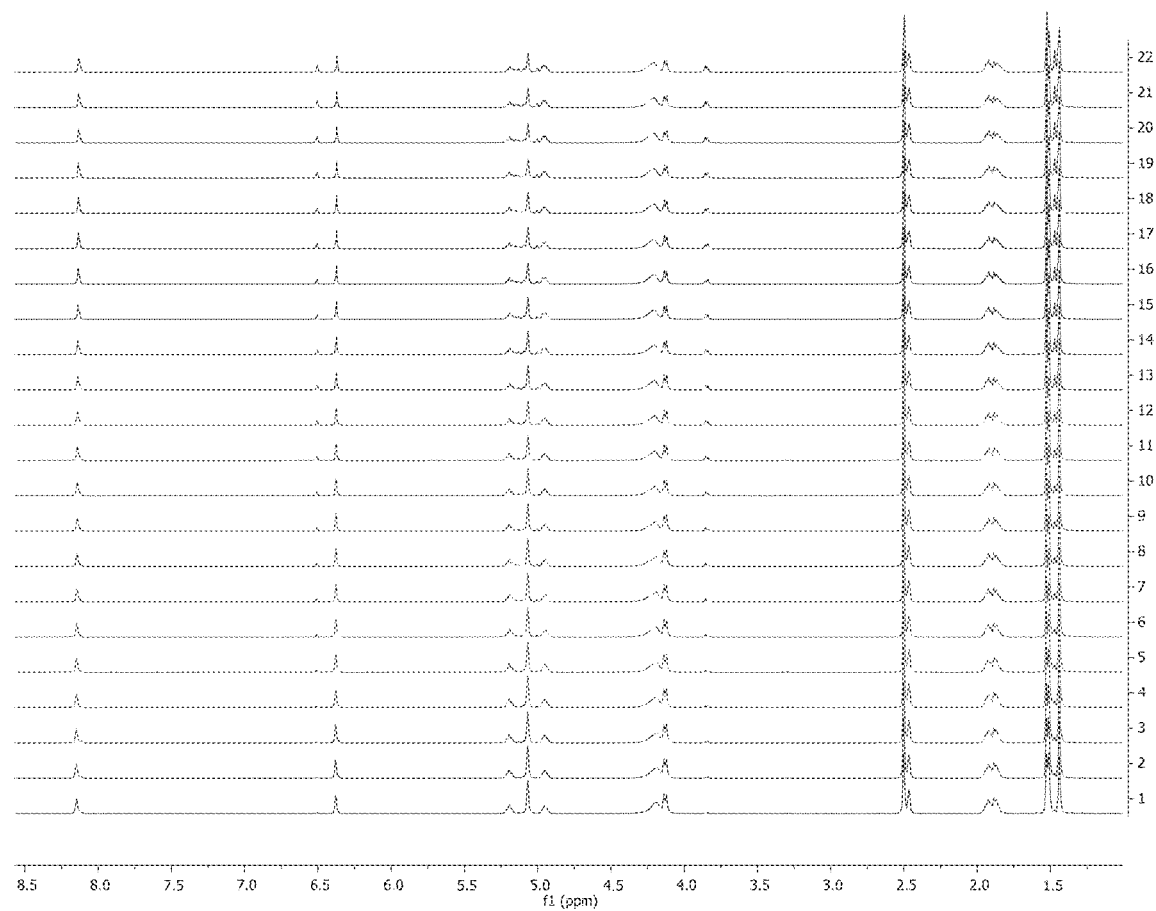
FIG. 7 is a stack plot for geranyl acetal showing the release of geraniol in 30% deuterium oxide in DMSO-$d_6$.
Figure 8:
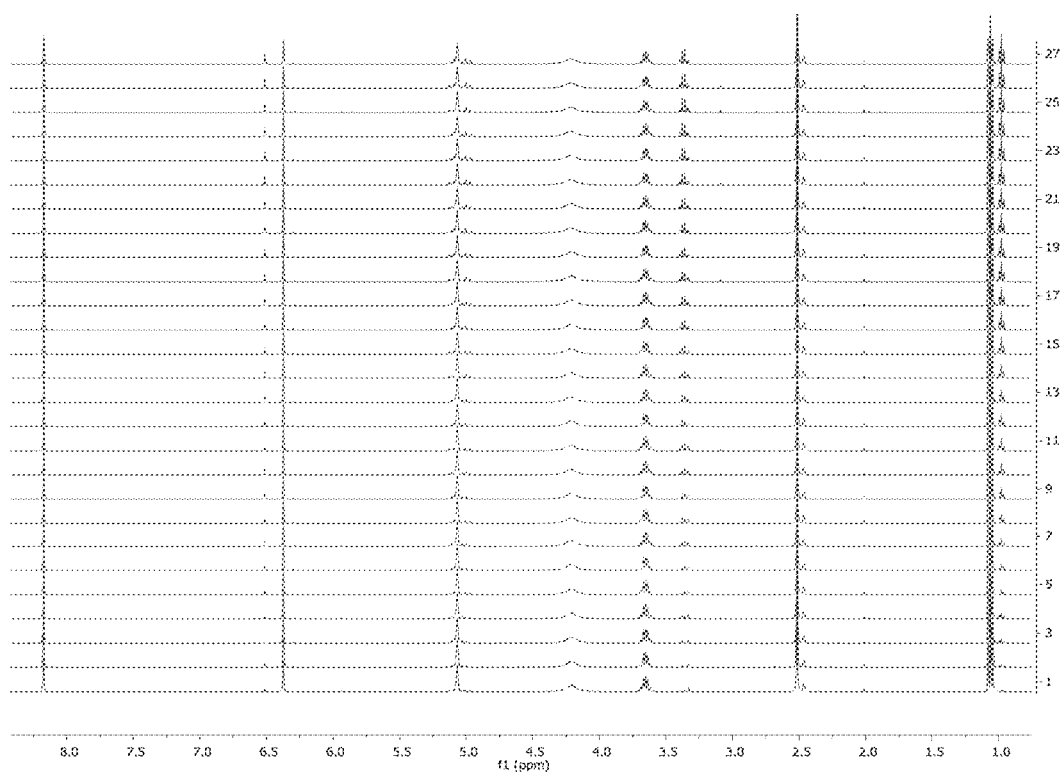
FIGS. 8-11 are stack plots showing release of ethanol in 20% $D_2O$, 35% $D_2O$, 50% $D_2O$, and 100% $D_2O$, respectively.
Figure 9:
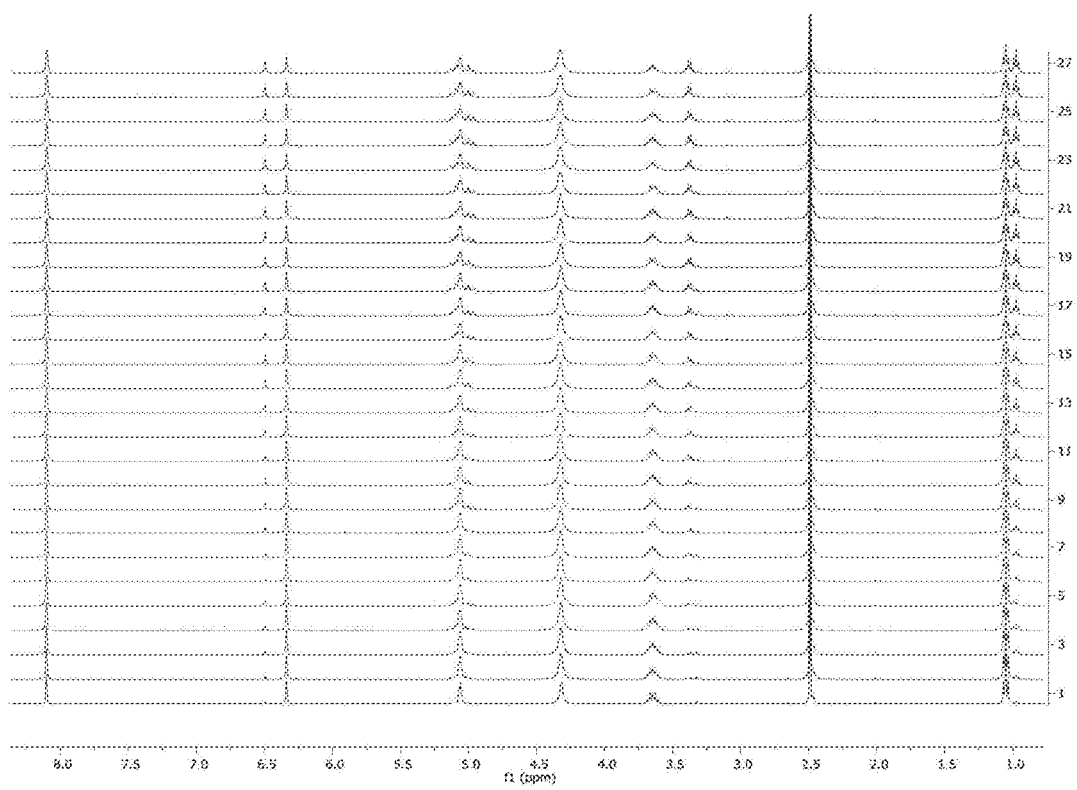
Figure 10:
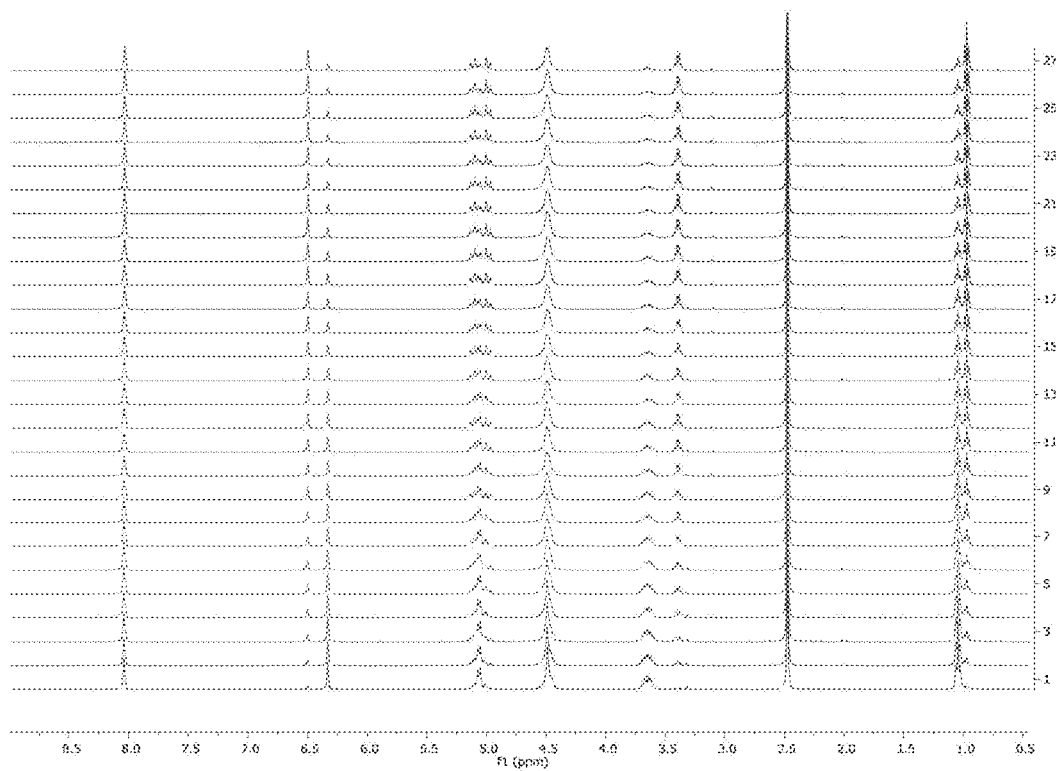
Figure 11:
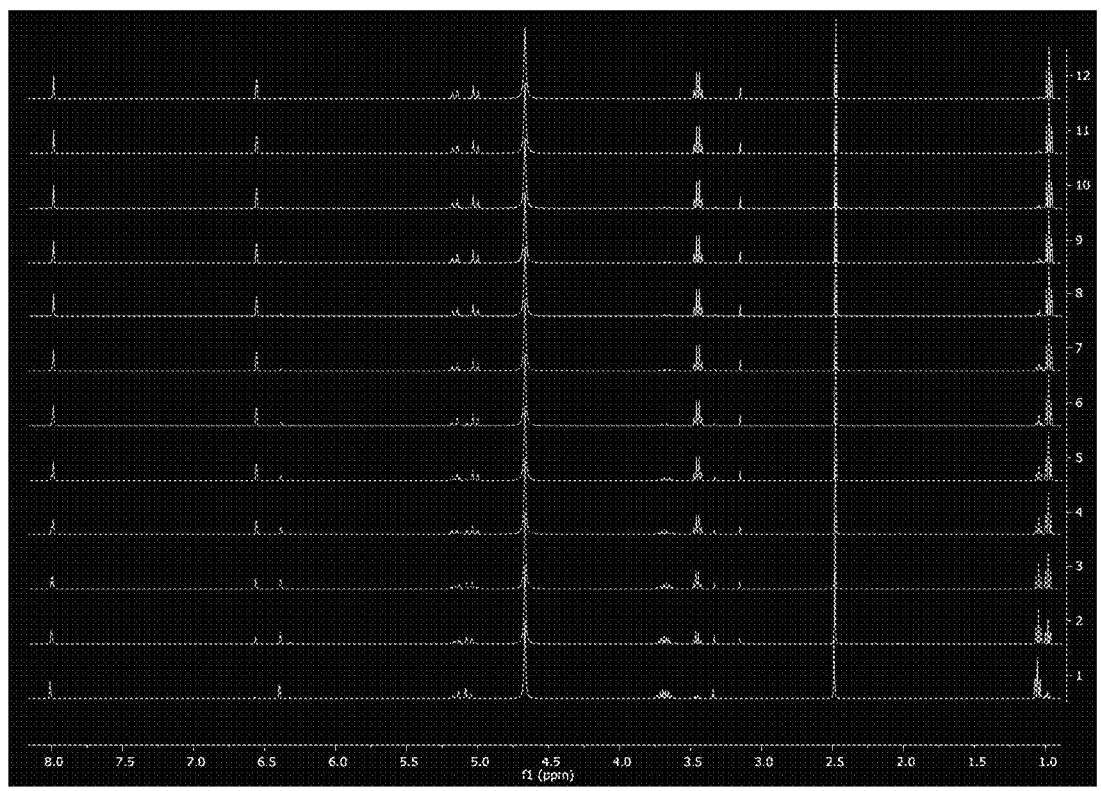
Figure 12A:
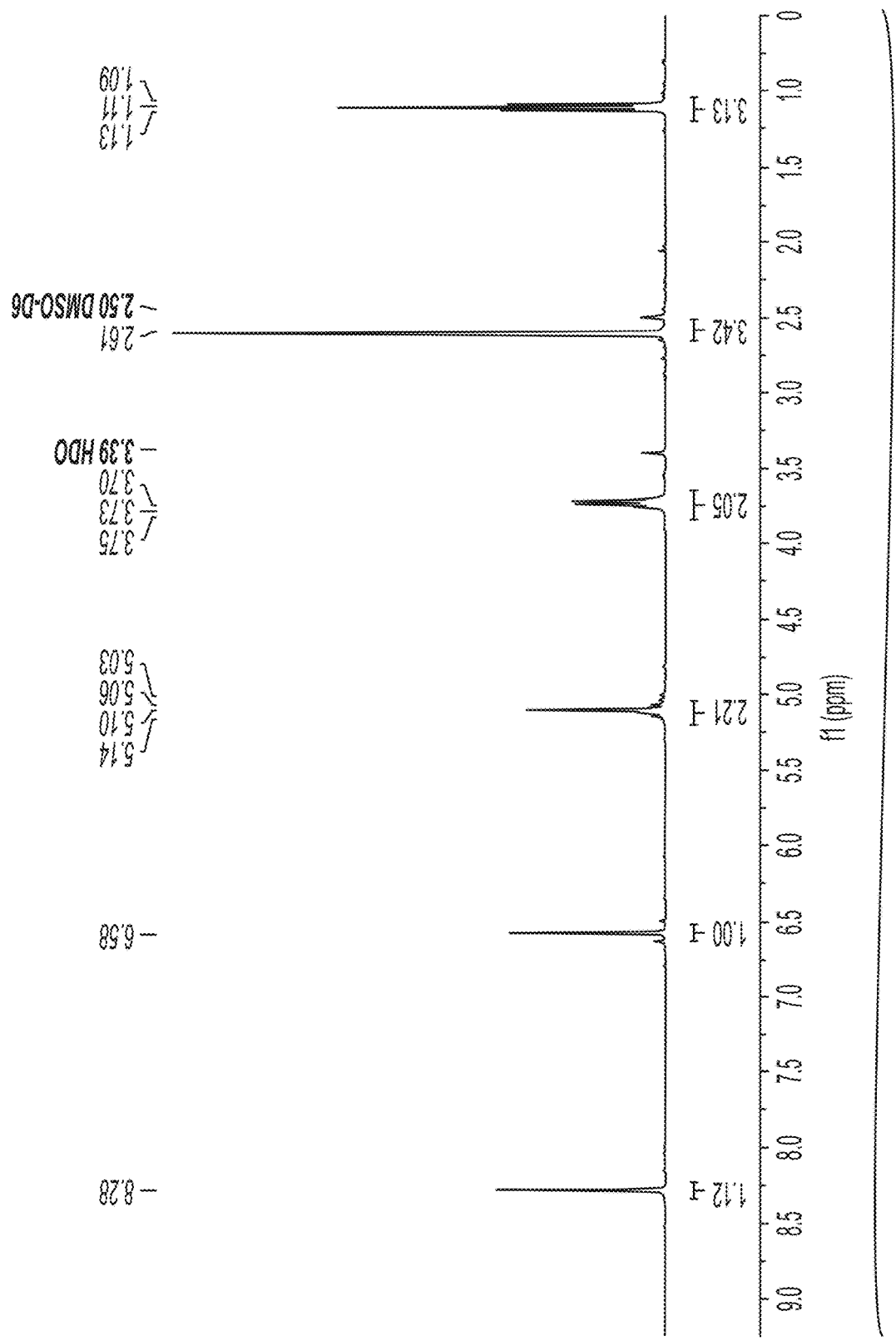
Figure 12B:
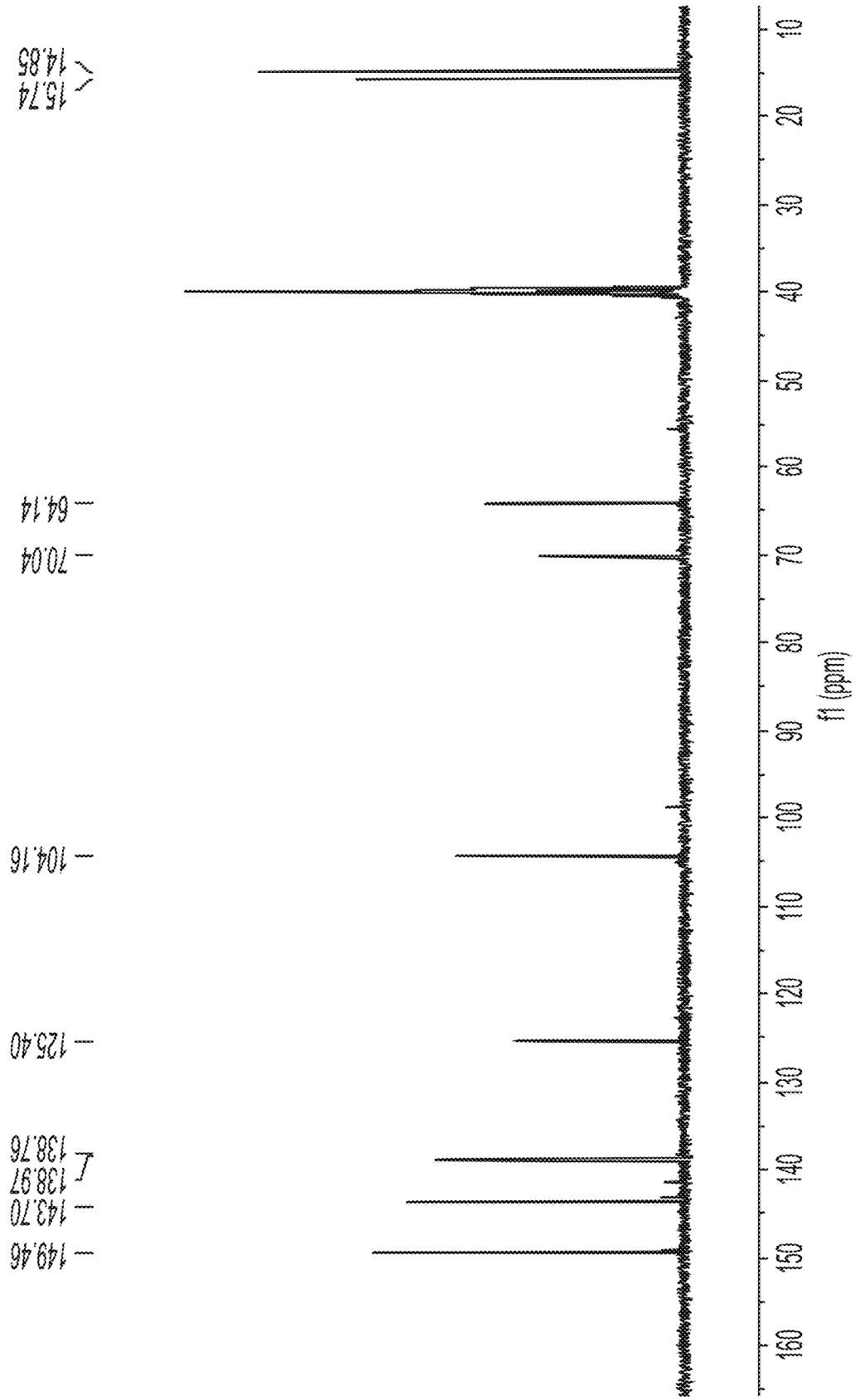
Figure 13A:
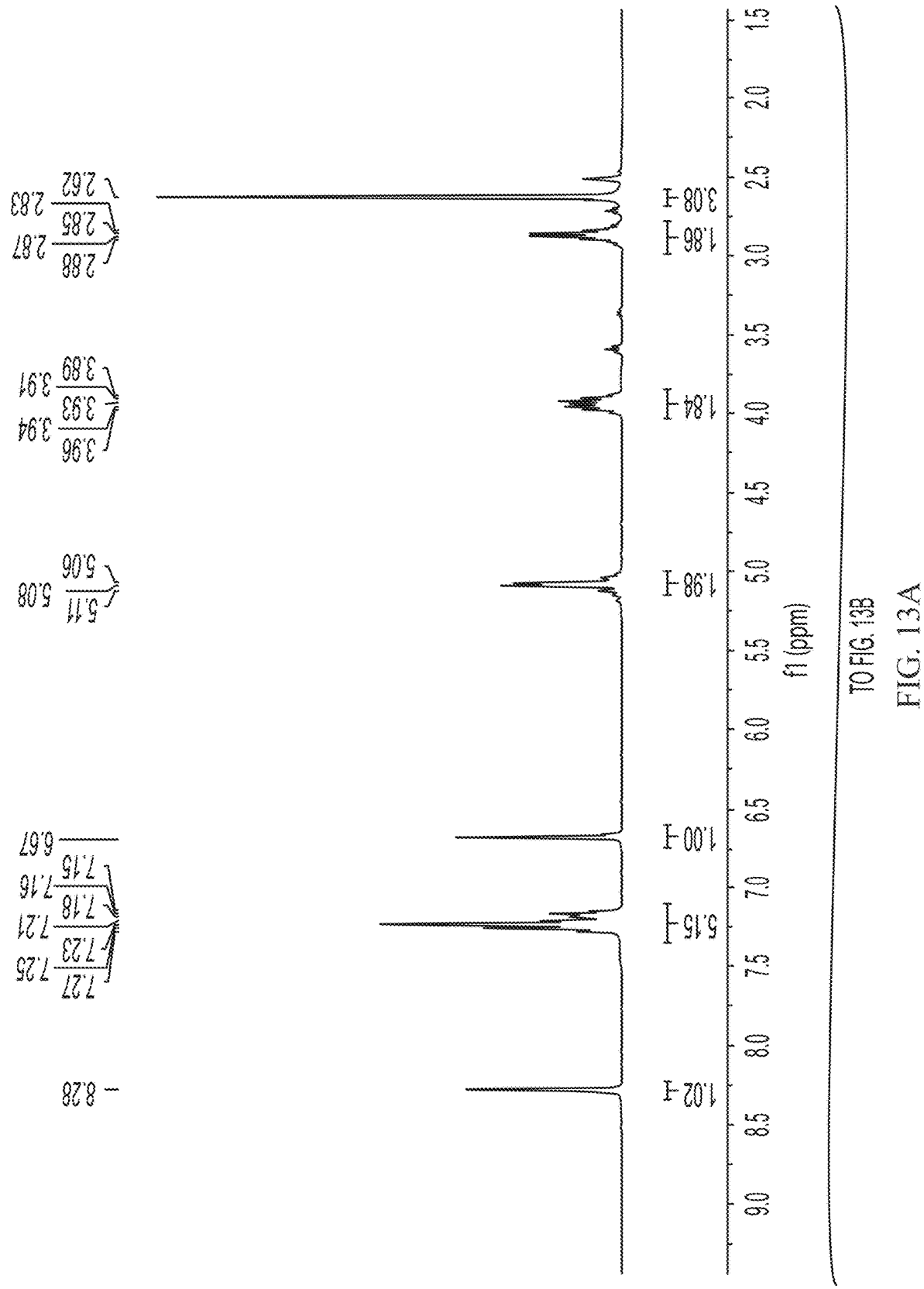
FIG. 13 contains $^1H$ and $^{13}C$ spectra of compound 3b.
Figure 13B:
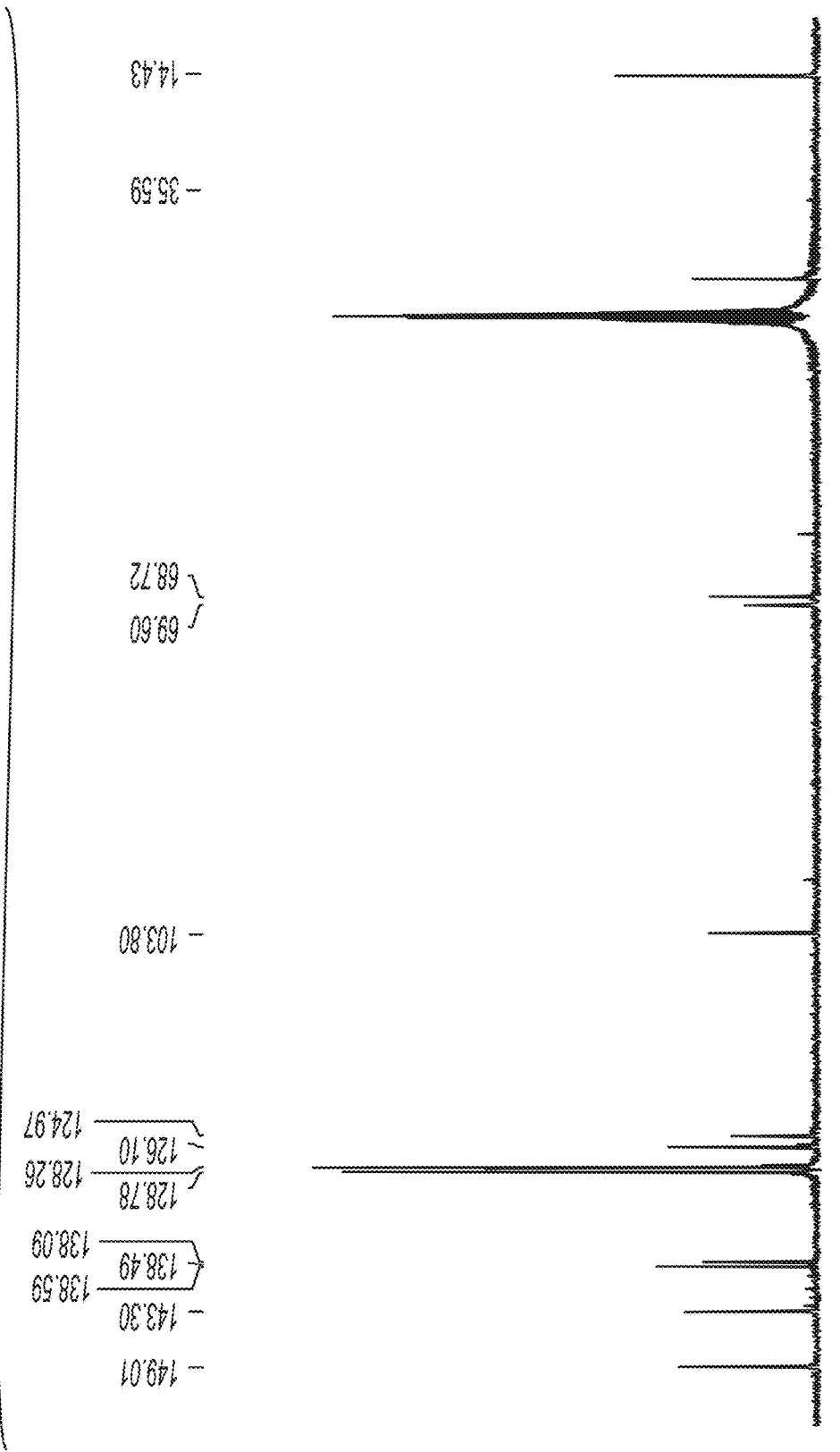
Figure 14A:
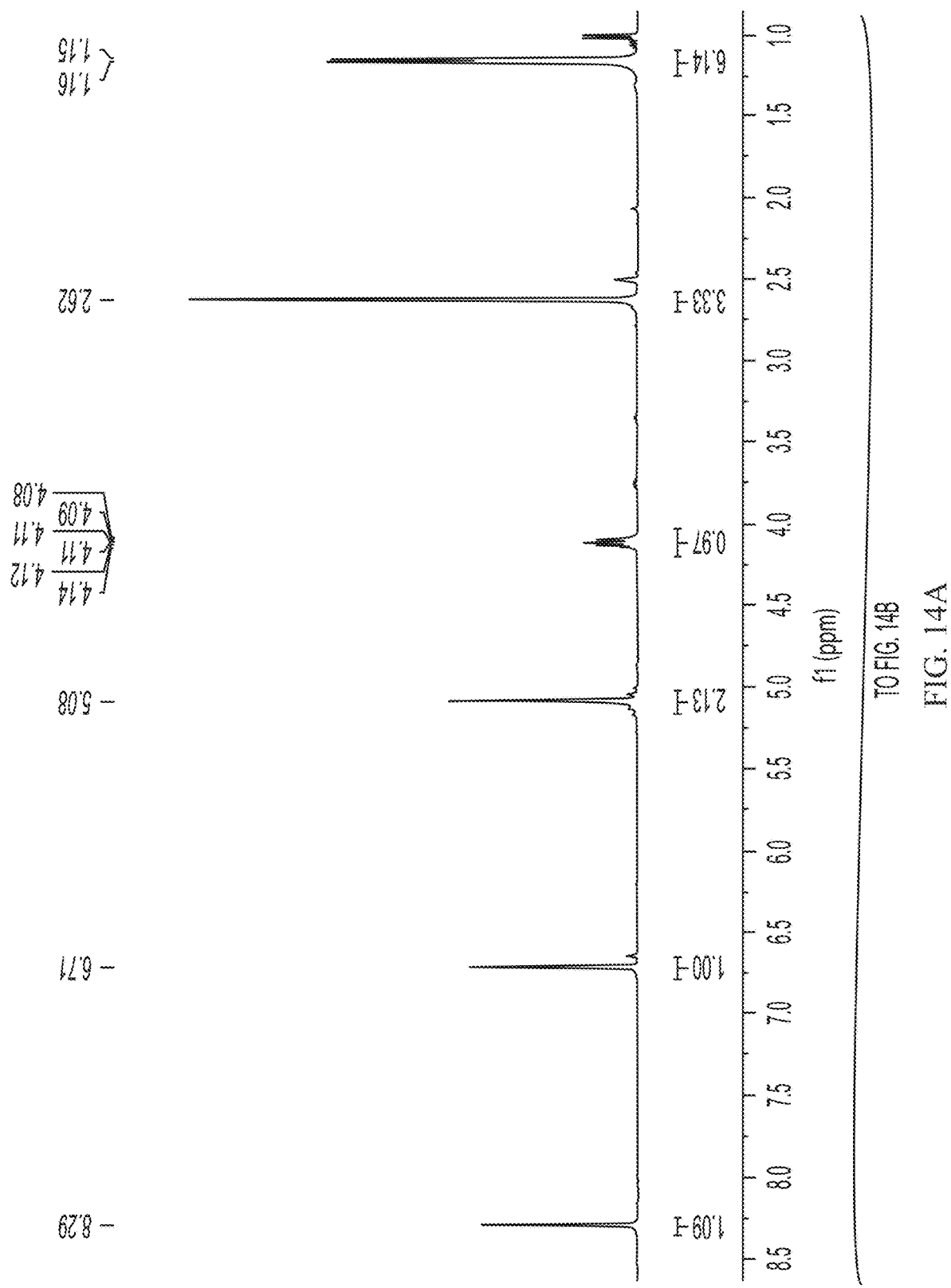
FIG. 14 contains $^1H$ and $^{13}C$ spectra of compound 3c.
Figure 14B:
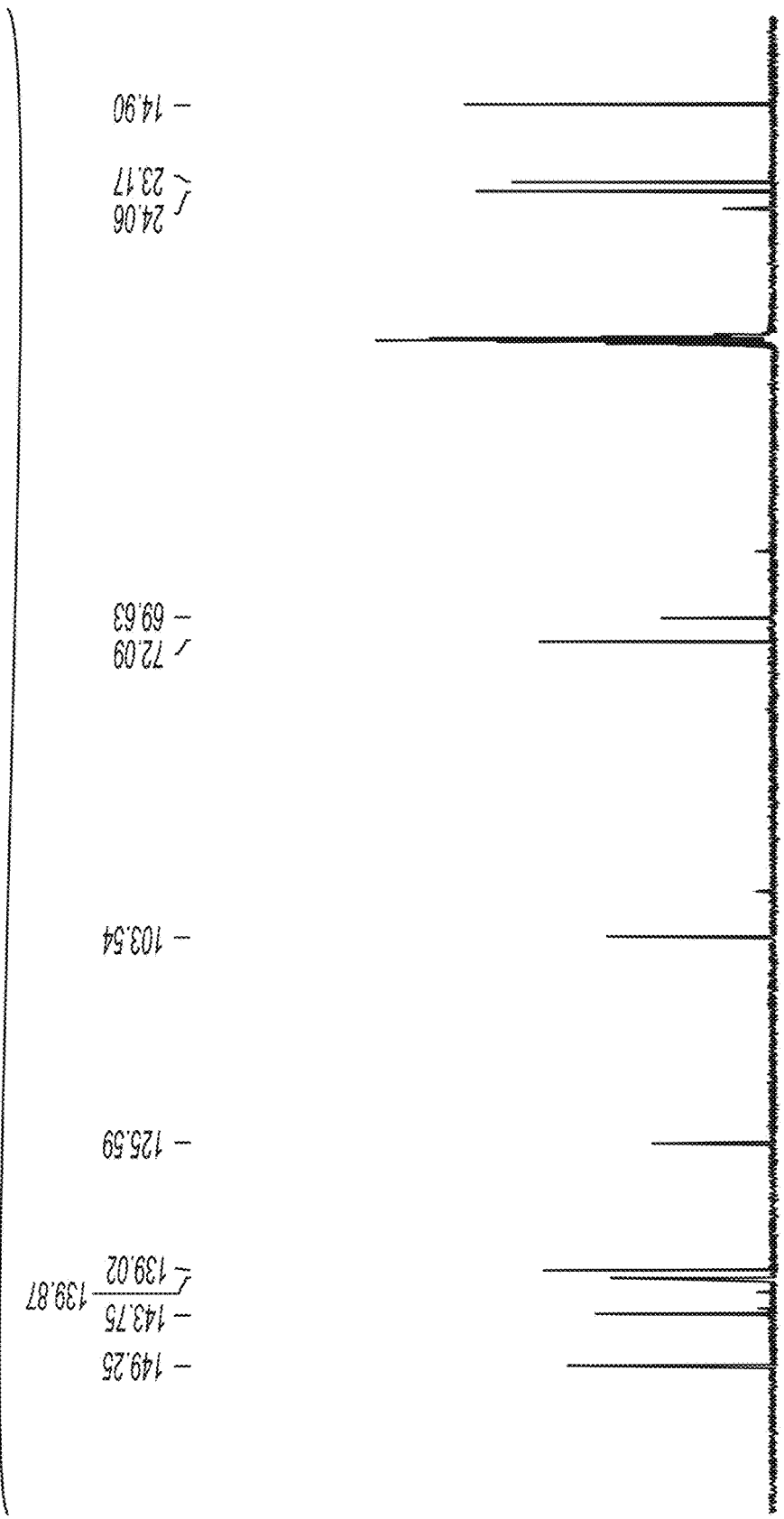
Figure 15A:
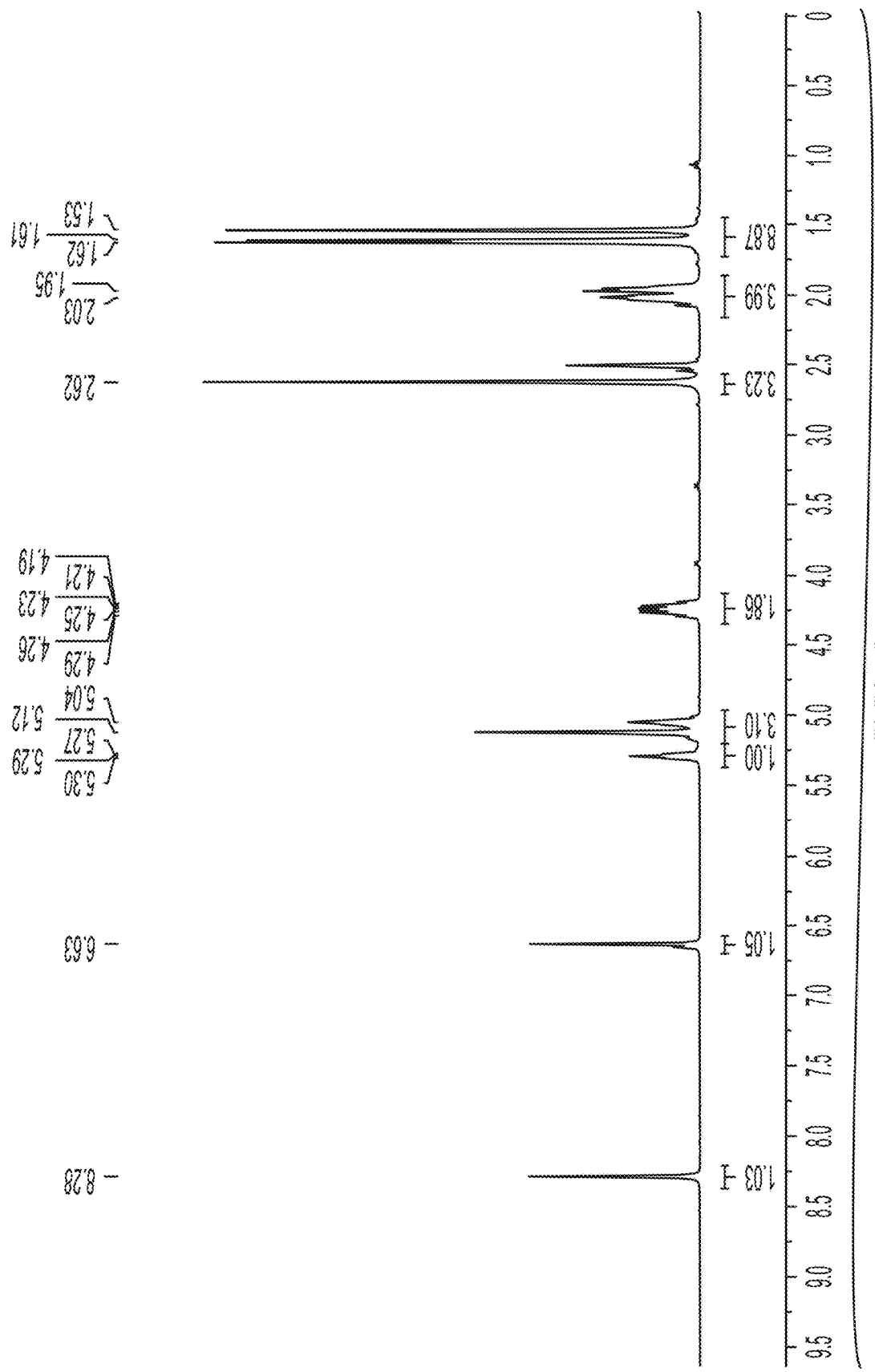
FIG. 15 contains $^1H$ and $^{13}C$ spectra of compound 3d.
Figure 15B:
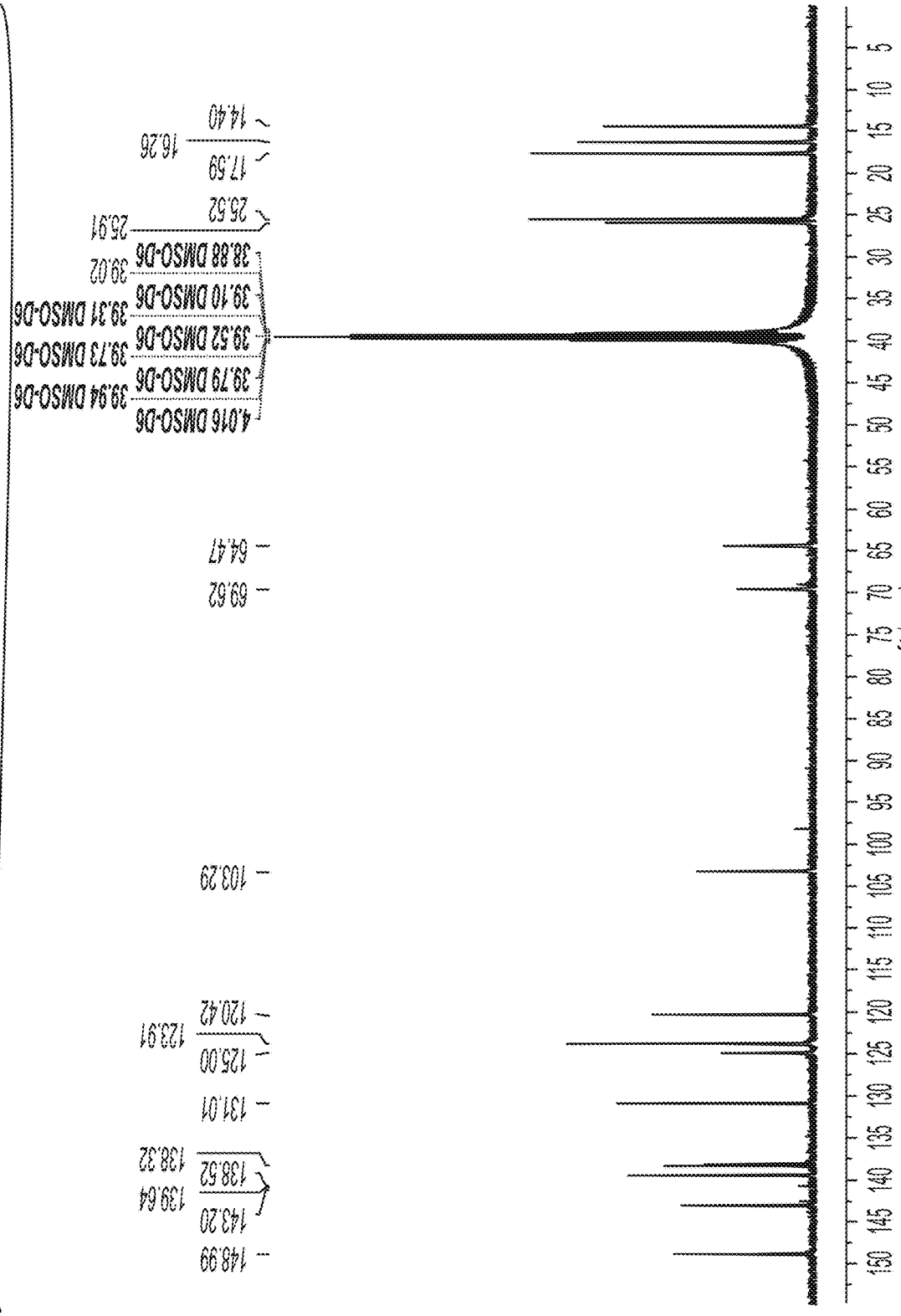

The rate of release for ethanol (blue), isopropanol (red), 2-phenylethanol (green), and geraniol (purple) were monitored at a 0.2 M concentration of 30% $D_2O$ in DMSO-$d_6$ from the respective pyridoxal acetal. As shown in FIG. 4 each acetal demonstrated linear controlled-release with ethanol providing the slowest release at 35% after 22 hours and isopropanol providing the highest release of 37% after 22 hours. In all cases, the acetals hydrolyze to release the target molecule and pyridoxal HCl quantitatively. Since other fragrance delivery systems can lose material in side reactions (H. Q. N. Gunaratne et al., Chem. Commun., 2015, 51, 4455), the high fidelity in the release for these alcohols is significant.

The following examples serve to illustrate certain aspects of the disclosure and should not be construed as limiting the claims. The contents of all references, pending patent applications and published patents, cited throughout this application are hereby expressly incorporated by reference.

EXAMPLES

General Information

Proton and carbon nuclear magnetic resonance spectra ($^1H$ and $^{13}C$ NMR) were recorded at 400 and 100 MHz, respectively, with solvent resonance as the internal standard ($^1H$ NMR: DMSO-$d_6$ at 2.500 ppm; $^{13}C$ NMR: DMSO-$d_6$ at 39.52 ppm). $^1H$ NMR data are reported as follows: chemical shift, multiplicity (s=singlet, d=doublet, dd=doublet of doublets, t=triplet, q=quartet, m=multiplet), coupling constants (Hz), and integration. Mass spectra were recorded on a high-resolution electrospray ionization quadrupole mass spectrometer. All reactions were carried out under air with magnetic stirring. Yield refers to isolated yield of analytically pure material. Yields are reported for a specific experiment and as a result may differ slightly from those found in the tables, which are averages of at least two experiments.

General Procedure for the Synthesis of the Pyridoxal Acetal Salts (3a-3c).

Pyridoxal HCl was added to the appropriate alcohol (0.5 M) and the solution was heated to 60° C. for 2 hours. The solution was then cooled to room temperature and either concentrated in vacuo (3a, 3c) or diluted with ether and allowed to crystallize in the freezer before being filtered to provide pure material (3b, 3d).

Analytical Data for Pyridoxal Acetal Salts (3a-3d)

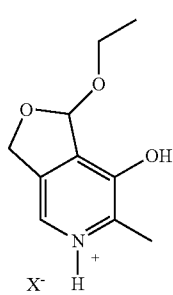

3a

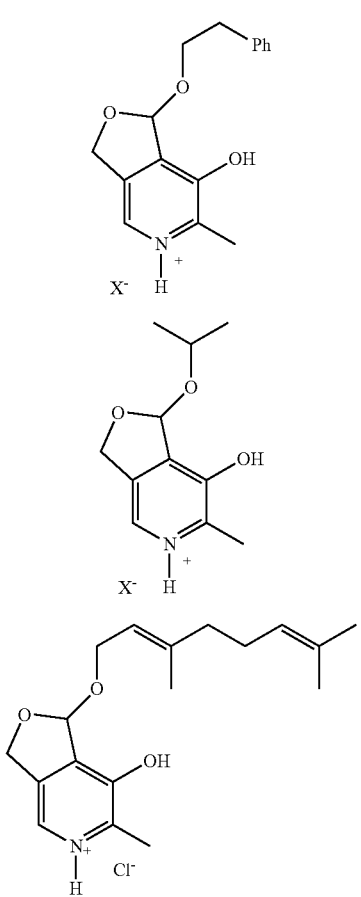

Example 1

1-ethoxy-7-hydroxy-6-methyl-1,3-dihydrofuro[3,4-c]pyridin-5-ium chloride (3a): The title compound was prepared according to the general procedure using pyridoxal HCl 1 (100 mg, 0.491 mmol, 1 equiv) in ethanol (1.0 mL, 0.5 M) affording 115 mg (99%) of the product as a white solid. Analytical Data for 3a: m.p.: 97-103° C. $^1$H NMR (400 MHz, DMSO-d$_6$) $\delta_H$ 12.05 (br. s, 1H), 8.28 (s, 1H), 6.58 (s, 1H), 5.14-5.03 (m, 2H), 3.75-3.70 (m, 2H) 2.61 (s, 3H), 1.11 (t, J=7.0 Hz, 3H) $^{13}$C NMR (100 MHz, CDCl$_3$): $\delta_C$ 149.5, 143.7, 139.0, 138.8, 125.4, 104.2, 70.0, 64.1, 15.7, 14.9.

Example 2

7-hydroxy-6-methyl-1-phenethoxy-1,3-dihydrofuro[3,4-c]pyridin-5-ium chloride (3b): The title compound was prepared according to the general procedure using pyridoxal HCl 1 (100 mg, 0.491 mmol, 1 equiv) in 2-phenylethanol (1.0 mL, 0.5 M) affording 133.4 mg (89%) of the product as a white solid. Analytical Data for 3b: m.p. 168-172° C. $^1$H NMR (400 MHz, DMSO-d$_6$): $\delta_H$ 12.09 (br. s, 1H), 8.28 (s, 1H), 7.27-7.15 (m, 5H), 6.67 (s, 1H), 5.11-5.06 (m, 2H), 3.96-3.89 (m, 2H), 2.88-2.83 (m, 2H), 2.62 (s, 3H); $^{13}$C NMR (100 MHz, DMSO-d$_6$): $\delta_C$ 149.0, 143.3, 138.6, 138.5, 138.1, 128.8, 128.3, 126.1, 124.97, 103.8, 69.6, 68.7, 35.6, 14.4.

Example 3

7-hydroxy-1-isopropoxy-6-methyl-1,3-dihydrofuro[3,4-c]pyridin-5-ium chloride (3c): The title compound was prepared according to the general procedure using pyridoxal HCl 1 (100 mg, 0.491 mmol, 1 equiv) in isopropanol (1.0 mL, 0.5 M) affording 120 mg (99%) of the product as a white solid. Analytical Data for 3c: m.p. 116-121° C. $^1$H NMR (400 MHz, DMSO-d$_6$): $\delta_H$ 1.92 (br. s, 1H), 8.29 (s, 1H), 6.71 (s, 1H), 5.08, (s, 2H), 4.14-4.08 (m, 1H), 2.62 (s, 3H), 1.16 (d, J=4.0 Hz, 6H) $^{13}$C NMR (100 MHz, CDCl$_3$): $\delta_C$ 149.3, 143.8, 139.9, 139.0, 125.6, 72.1, 69.6, 24.1, 23.2.

Example 4

(E)-1-((3,7-dimethylocta-2,6-dien-1-yl)oxy)-7-hydroxy-6-methyl-1,3-dihydrofuro[3,4-c]pyridin-5-ium chloride (3d): The title compound was prepared according to the general procedure using pyridoxal HCl 1 (100 mg, 0.491 mmol, 1 equiv) in geraniol (1.0 mL 0.5 M) and in DMSO (0.02 mL, 25 M) to aid with solubility affording 123 mg (73%) of the product as a white solid. Analytical data for 3d: m.p. 140-142° C. $^1$H NMR (400 MHz, DMSO-d$_6$): $\delta_H$ 12.04 (br. s, 1H), 8.28 (s, 1H), 6.63 (s, 1H), 5.30-5.27 (s, 1H), 5.12-5.04 (m, 3H), 4.29-4.19 (m, 2H), 2.62 (s, 3H), 2.03-1.95 (m, 4H), 1.62 (s, 3H), 1.61 (s, 3H), 1.53 (s, 3H) $^{13}$C NMR (100 MHz, CDCl$_3$): $\delta_C$ 149.0, 143.2, 139.6, 138.5, 138.3, 131.0, 125.0, 123.9, 120.4, 103.3, 69.6, 64.5, 39.0, 25.9, 25.5, 17.6, 16.3, 14.4.

Time-Dependent Stack Plots of Acetal Cleavage

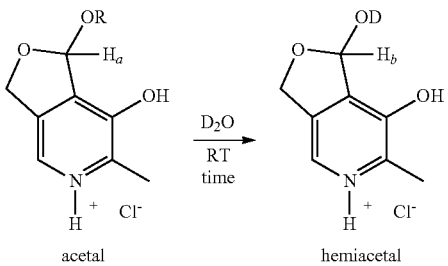

The acetal cleavage was measured by comparing the integration of H$_a$ to H$_b$ whereas H$_b$/(H$_a$+H$_b$) provides the percent completion for the acetal cleavage for 3a and 3b. The stack plots in FIGS. 7-11 provide a visual counterpart to the graphs. 3c had some overlap between H$_a$ and H$_b$ so the fully separated methyl groups of the isopropyl were integrated instead.

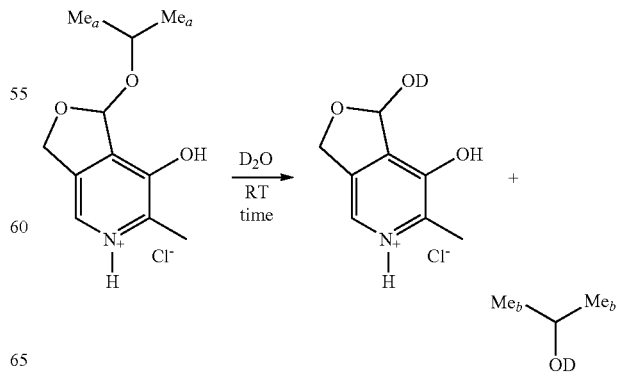

Conditions for the Kinetic Reaction Profile for the Release of Ethanol 3a (0.1636 mmol) was dissolved in 0.4 mL of DMSO-$d_6$ (except for 100% $D_2O$) and varying amounts of $D_2O$ were added, as shown in the table below (see corresponding stack plots in FIGS. 7-11).

| % $D_2O$ | 100% | 50% | 35% | 20% |
|---|---|---|---|---|
| $D_2O$ Added | 0.8 mL | 0.4 mL | 0.23 mL | 0.1 mL |
| Final Molarity | 0.2M | 0.2M | 0.25M | 0.3M |

What is claimed is:

1. A compound of formula I:

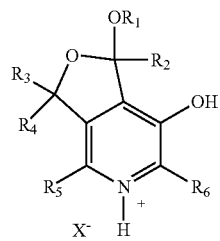

wherein:
$R_1$ is a C8-C20 hydrocarbyl group, and $R_2$, $R_3$, $R_4$, $R_5$, and $R_6$ are independently hydrogen or a C1-C10 hydrocarbyl group; and
X is a counterion,
or the corresponding free base.

2. The compound of claim 1, wherein $R_6$ is C1-C6 straight, branched, or cyclic alkyl.

3. The compound of claim 2, wherein $R_6$ is methyl.

4. The compound of claim 3, wherein the compound is of formula II:

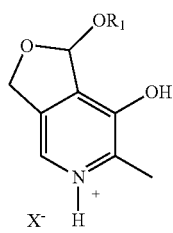

wherein:
$R_1$ is a C8-C20 hydrocarbyl group.

5. The compound of claim 1, wherein X is $HSO_4$, $H_2PO_4$, F, Cl, Br, I, or OH.

6. The compound of claim 1, wherein $R_1$ is C8-C10 alkyl that is unsubstituted or substituted with one or more aryl groups, wherein each aryl group is unsubstituted or substituted with one or more C1-C6 straight, branched, or cyclic alkyl groups.

7. The compound of claim 6, wherein $R_1$ is substituted with one or more substituted or unsubstituted phenyl groups.

8. The compound of claim 7, wherein each phenyl is independently unsubstituted or substituted at any position with a C1-C6 straight, branched, or cyclic alkyl group or with a phenyl group.

9. The compound of claim 8, wherein the compound is:

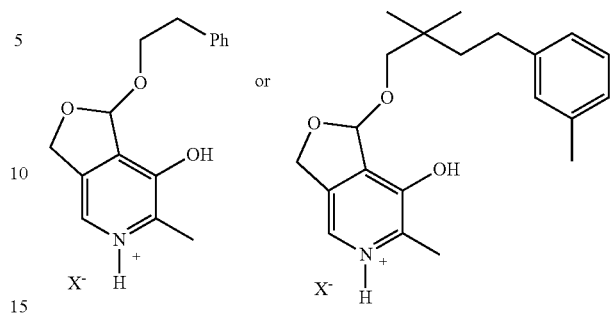

or the corresponding free base.

10. The compound of claim 1, wherein $R_1$ comprises one or more ethenyl groups.

11. The compound of claim 10, wherein the compound is:

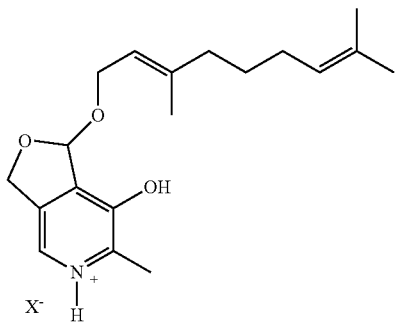

or the corresponding free base.

12. The compound of claim 1, wherein $R_1$ is a C8-C15 hydrocarbyl group.

13. The compound of claim 1, wherein $R_1$ is a C8-C13 hydrocarbyl group.

14. A compound of formula I:

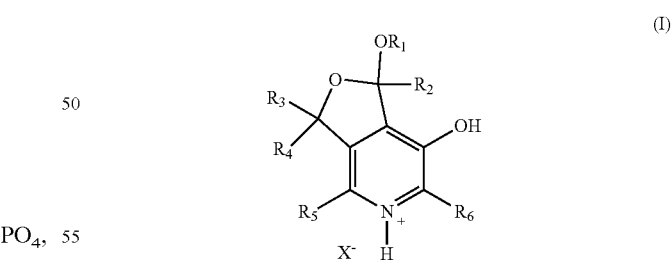

wherein:
$R_1$ is a C1-C20 hydrocarbyl group, and $R_2$, $R_3$, $R_4$, $R_5$, and $R_6$ are independently hydrogen or a C1-C10 hydrocarbyl group; and
X is a counterion,
or the corresponding free base,
wherein when $R_6$ is methyl and $R_2$, $R_3$, $R_4$, and $R_5$ are each hydrogen, then $R_1$ is not C1-C4 alkyl or n-hexyl.

15. A compound as shown below, wherein X is a counterion, or the corresponding free base:
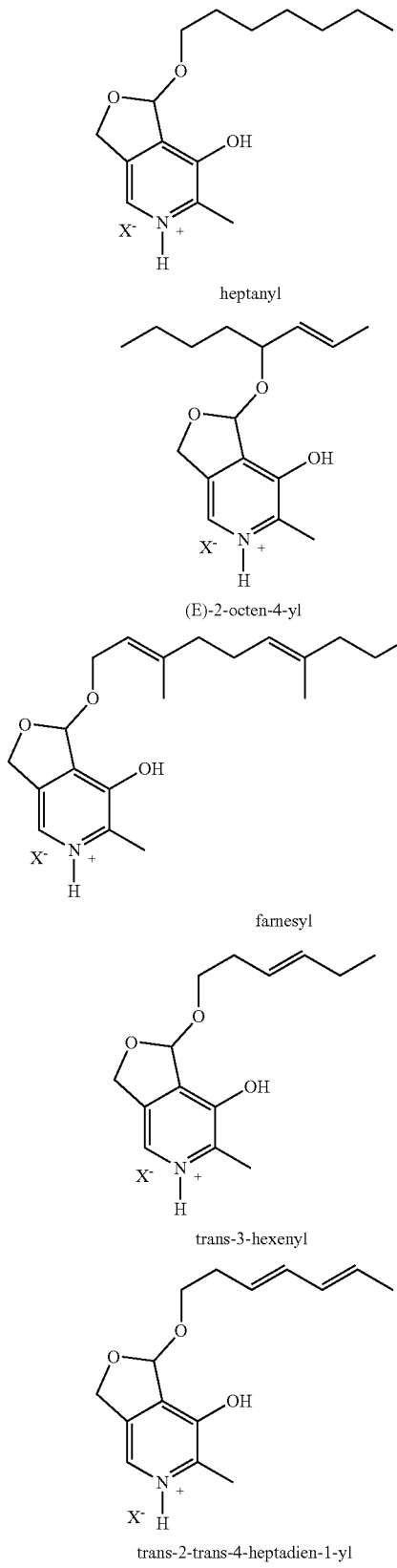
heptanyl
(E)-2-octen-4-yl
farnesyl
trans-3-hexenyl
trans-2-trans-4-heptadien-1-yl
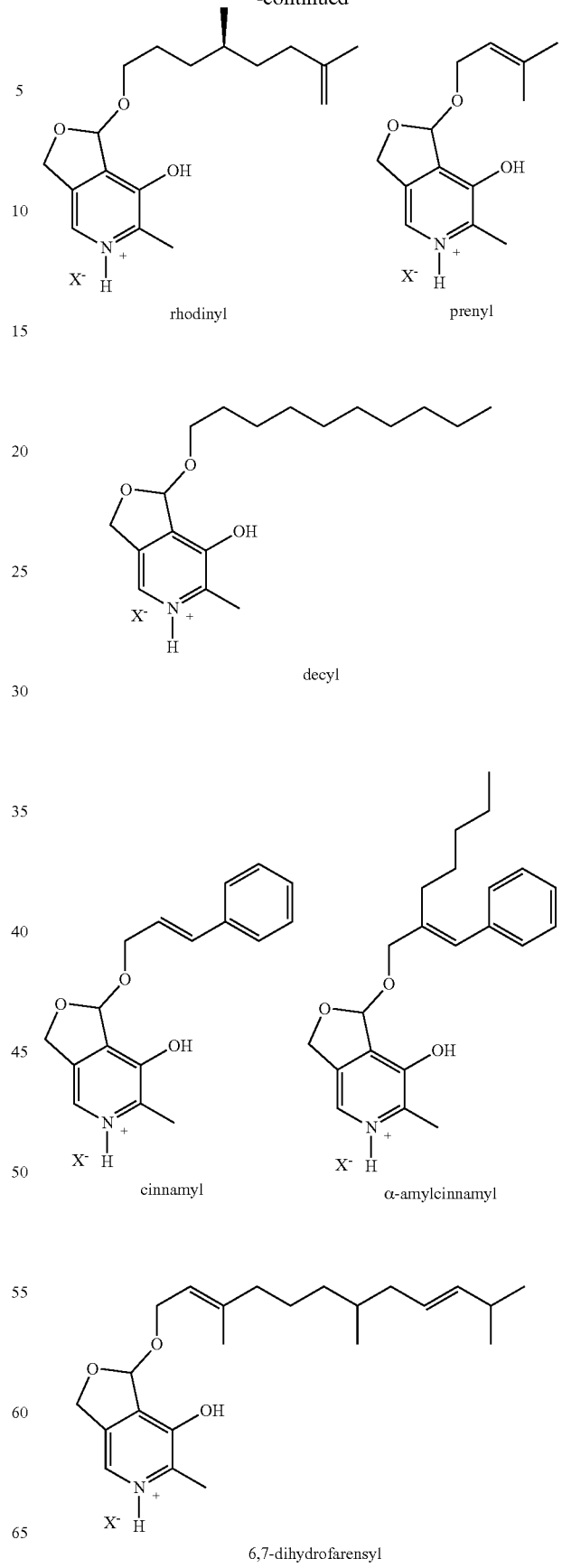
rhodinyl
prenyl
decyl
cinnamyl
α-amylcinnamyl
6,7-dihydrofarensyl

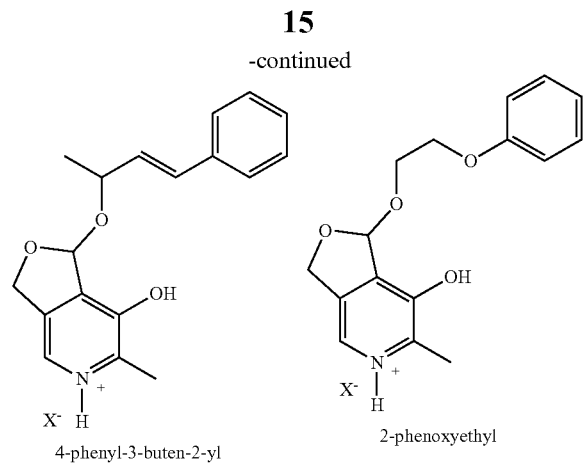

4-phenyl-3-buten-2-yl 2-phenoxyethyl

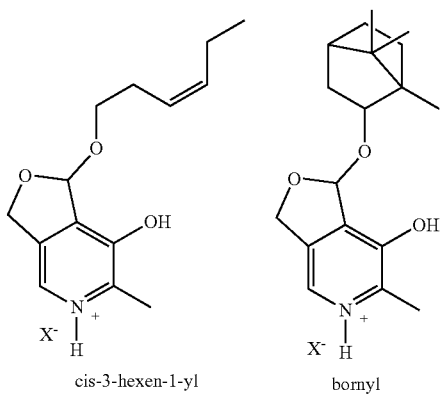

cis-3-hexen-1-yl bornyl

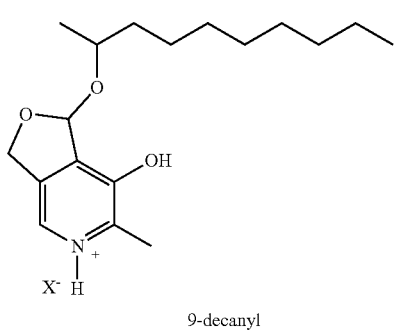

9-decanyl

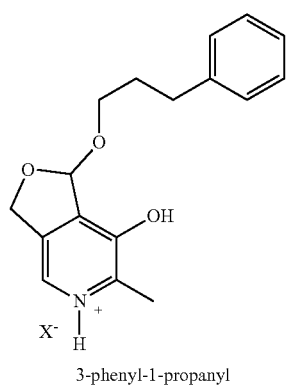

3-phenyl-1-propanyl

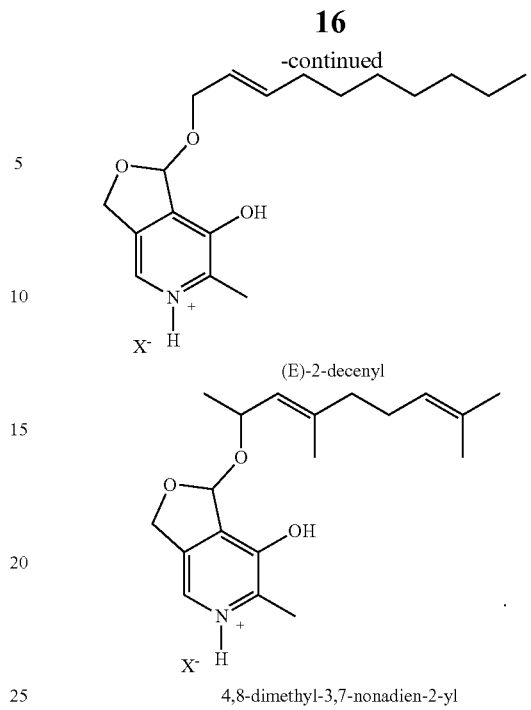

(E)-2-decenyl or 4,8-dimethyl-3,7-nonadien-2-yl

16. A composition comprising the compound of claim 1 and a carrier, adjuvant, or active agent suitable for skin care, hair care, or cosmetics.

17. The composition of claim 16 in the form of an emulsion.

18. A method of providing a scent to a subject, comprising administering an effective amount of a composition according to claim 16 to a subject.

19. The method of claim 18, wherein the scent is released in a timed-release manner.

20. A chewing gum comprising (a) a gum base, (b) a compound according to claim 1, and (c) optionally flavors.

21. The chewing gum of claim 20, wherein the gum base is a chewable, substantially water insoluble base.

22. A method to confer, improve, enhance or modify a taste or flavor property of a composition or article, comprising adding to the composition or article a flavor effective amount of a compound or mixture of compounds according to claim 1.

23. A chewing gum comprising (a) a gum base, (b) a compound according to claim 15, and (c) optionally flavors.

24. The compound of claim 5, wherein X is an organic counterion.

25. The compound of claim 24, wherein X is a sulfosuccinate or a carboxylate.

26. The compound of claim 25, wherein X is docusate or cinnamate.

27. The compound of claim 15, wherein X is $HSO_4$, $H_2PO_4$, F, Cl, Br, I, or OH.

28. The compound of claim 15, wherein X is an organic counterion.

29. The compound of claim 28, wherein X is a sulfosuccinate or a carboxylate.

30. The compound of claim 29, wherein X is docusate or cinnamate.

31. The chewing gum of claim 21, wherein the gum base is chicle, sorva, guttakay, jelutong, polyvinyl acetate, a synthetic polymer, or mixtures thereof.

32. The chewing gum of claim 20, comprising wintergreen, spearmint, peppermint, birch, anise, fruit flavors, or mixtures thereof.

33. The chewing gum of claim 23, comprising wintergreen, spearmint, peppermint, birch, anise, fruit flavors, or mixtures thereof.

\* \* \* \* \*